(12) United States Patent
Penake et al.

(10) Patent No.: US 9,711,063 B2
(45) Date of Patent: Jul. 18, 2017

(54) METHODS AND DEVICES FOR INTRAORAL TACTILE FEEDBACK

(71) Applicant: ARTICULATE TECHNOLOGIES, INC., San Francisco, CA (US)

(72) Inventors: David A. Penake, San Mateo, CA (US); Alexey Salamini, San Francisco, CA (US); Gordy Rogers, Brooklyn, NY (US); Joe Watson, New York, NY (US)

(73) Assignee: Speech Buddies, Inc., San Francisco, CA (US)

( * ) Notice: Subject to any disclaimer, the term of this patent is extended or adjusted under 35 U.S.C. 154(b) by 0 days.

(21) Appl. No.: 15/046,415

(22) Filed: Feb. 17, 2016

(65) Prior Publication Data

US 2016/0163227 A1    Jun. 9, 2016

Related U.S. Application Data

(63) Continuation of application No. 14/274,223, filed on May 9, 2014, now abandoned, which is a continuation
(Continued)

(51) Int. Cl.
*G09B 19/04* (2006.01)
*A61F 5/58* (2006.01)
(Continued)

(52) U.S. Cl.
CPC .............. *G09B 19/04* (2013.01); *A61F 5/58* (2013.01); *A61B 5/228* (2013.01); *A61B 5/486* (2013.01);
(Continued)

(58) Field of Classification Search
CPC ........... A61F 5/58; G09B 19/04; G09B 19/06; A61B 5/228; A61B 5/682; A61B 5/486; A63B 23/032; A63B 2071/0625
(Continued)

(56) References Cited

U.S. PATENT DOCUMENTS

| 779,360 A | 1/1905 | Grumman ....................... 600/24 |
| 1,327,407 A | 1/1920 | Rogers |

(Continued)

FOREIGN PATENT DOCUMENTS

| DE | 202 06 571 U1 | 9/2002 |
| JP | 2004-093723 A | 3/2004 |

(Continued)

OTHER PUBLICATIONS

Kaczmarek et al., "Electrotactile and Vibrotactile Displays for Sensory Substitution Systems," IEEE Transactions on Biomedical Engineering, 38(1):1-16, Jan. 1991.
(Continued)

*Primary Examiner* — Jack Yip
(74) *Attorney, Agent, or Firm* — Winston & Strawn LLP

(57) ABSTRACT

The present invention is directed to methods and devices for teaching the proper configuration of the oral articulators, particularly the tongue, corresponding to particular speech sounds by providing intraoral tactile feedback. Intraoral tactile feedback is achieved by placing nodes in the oral cavity of the patient in locations corresponding to the proper lingual position required to produce a target sound. These nodes facilitate identification of the appropriate lingual position corresponding to a target speech sound by providing tactile differentiation when the target sound is properly produced.

9 Claims, 33 Drawing Sheets

Related U.S. Application Data of application No. 12/357,239, filed on Jan. 21, 2009, now Pat. No. 8,740,622.

(60) Provisional application No. 61/011,364, filed on Jan. 17, 2008.

(51) Int. Cl.

| | |
|---|---|
| A63B 23/03 | (2006.01) |
| A61B 5/00 | (2006.01) |
| A61B 5/22 | (2006.01) |
| A63B 71/06 | (2006.01) |
| G09B 19/06 | (2006.01) |

(52) U.S. Cl.
CPC .............. *A61B 5/682* (2013.01); *A63B 23/032* (2013.01); *A63B 2071/0625* (2013.01); *G09B 19/06* (2013.01)

(58) Field of Classification Search
USPC .................................. 434/185, 157; 600/590
See application file for complete search history.

(56) References Cited

U.S. PATENT DOCUMENTS

| | | | |
|---|---|---|---|
| 2,098,867 A | 11/1937 | Glisson | 128/137 |
| D160,490 S | 10/1950 | Gee | D83/1 |
| 2,549,398 A | 4/1951 | Stelz | 128/1 |
| 2,818,065 A | 12/1957 | Freed | 128/137 |
| 3,014,286 A | 12/1961 | Hricak | 424/157 |
| 3,401,685 A | 9/1968 | Staub | 128/24 |
| 3,556,093 A | 1/1971 | Quick | 128/137 |
| 3,867,770 A | 2/1975 | Davis | 434/185 |
| 3,983,865 A | 10/1976 | Shepard | 128/2.1 |
| 4,112,596 A | 9/1978 | Fletcher | 35/35 R |
| 4,287,895 A | 9/1981 | Hori | 128/777 |
| 4,310,002 A | 1/1982 | Takinishi et al. | 128/642 |
| 4,334,542 A | 6/1982 | Takinishi et al. | 128/642 |
| 4,629,424 A | 12/1986 | Lauks et al. | 433/6 |
| 4,697,601 A | 10/1987 | Durkee et al. | 128/777 |
| 4,718,662 A | 1/1988 | North | 272/95 |
| 4,723,910 A | 2/1988 | Keller | 433/7 |
| 5,213,553 A | 5/1993 | Light | 482/11 |
| 5,257,930 A | 11/1993 | Blakeley | 433/6 |
| 5,401,234 A | 3/1995 | Libin | 600/24 |
| 5,452,727 A | 9/1995 | Tura et al. | 128/777 |
| 5,507,648 A | 4/1996 | Knopf | 434/185 |
| 5,609,161 A | 3/1997 | Tura et al. | 128/777 |
| 5,689,246 A | 11/1997 | Dordick et al. | 340/825.19 |
| 5,735,772 A | 4/1998 | Schiavoni | 482/11 |
| 5,794,203 A | 8/1998 | Kehoe | 704/271 |
| 5,954,673 A | 9/1999 | Staehlin et al. | 600/590 |
| 6,190,335 B1 | 2/2001 | Howard et al. | 600/590 |
| 6,430,450 B1 | 8/2002 | Bach-y-Rita et al. | 607/134 |
| 6,511,441 B1 | 1/2003 | Wakumoto et al. | 600/590 |
| 6,598,006 B1 | 7/2003 | Honda et al. | 702/116 |
| 6,632,095 B2 | 10/2003 | Ryan | 434/185 |
| 6,702,765 B2 | 3/2004 | Robbins et al. | 600/590 |
| 6,971,993 B2 | 12/2005 | Fletcher | 600/587 |
| 6,974,424 B2 | 12/2005 | Fletcher | 600/587 |
| 7,083,548 B1 | 8/2006 | Moore et al. | 482/11 |
| 7,214,064 B1 | 5/2007 | Hall | 434/185 |
| 7,238,145 B2 | 7/2007 | Robbins et al. | 482/11 |
| 7,438,667 B2 | 10/2008 | Robbins et al. | 482/11 |
| 7,676,372 B1 | 3/2010 | Oba | 704/271 |
| 7,935,065 B2 | 5/2011 | Martin et al. | 600/590 |
| 7,999,857 B2 | 8/2011 | Bunn et al. | 348/211.1 |
| 2002/0087103 A1 | 7/2002 | Fletcher | 600/590 |
| 2002/0087322 A1 | 7/2002 | Fletcher | 704/270 |
| 2003/0078521 A1 | 4/2003 | Robbins et al. | 600/587 |
| 2003/0121521 A1 | 7/2003 | Hipolito et al. | 128/207.14 |
| 2004/0038188 A1 | 2/2004 | Lee | 434/185 |
| 2006/0028556 A1 | 2/2006 | Bunn et al. | 348/211.99 |
| 2006/0282010 A1 | 12/2006 | Martin et al. | 600/560 |
| 2007/0037665 A1 | 2/2007 | Robbins et al. | 482/11 |
| 2007/0168187 A1 | 7/2007 | Fletcher et al. | 704/209 |
| 2007/0225122 A1 | 9/2007 | Robbins et al. | 482/11 |
| 2008/0183107 A1 | 7/2008 | Miller et al. | 600/590 |
| 2008/0228239 A1 | 9/2008 | Tyler et al. | 607/45 |
| 2008/0271590 A1 | 11/2008 | Lemons | 84/483.2 |
| 2008/0286731 A1 | 11/2008 | Rolstone | 434/157 |
| 2009/0286199 A1 | 11/2009 | Creasman et al. | 433/141 |
| 2011/0202111 A1 | 8/2011 | Dillon et al. | 607/57 |
| 2011/0224287 A1 | 9/2011 | Tully et al. | 514/44 R |

FOREIGN PATENT DOCUMENTS

| | | |
|---|---|---|
| JP | 2004-272188 A | 9/2004 |
| KR | 10-2006-0002632 A | 1/2006 |

OTHER PUBLICATIONS

Tiede et al., "A New Approach to Pressure-Sensitive Palatography Using a Capacitive Sensing Device," Proceedings of the 15th International Congress of Phonetic Sciences, Barcelona, Spain, Aug. 3-9, 2003.
International Search Report and Written Opinion, Appl. No. PCT/US2009/031584, Sep. 7, 2009.
U.S. Appl. No. 12/357,239, Non-Final Rejection, Jun. 18, 2012.
U.S. Appl. No. 12/357,239, Final Rejection, Nov. 23, 2012.
U.S. Appl. No. 12/357,239, Advisory Action, Mar. 29, 2013.
U.S. Appl. No. 12/357,239, Non-Final Rejection, Jun. 27, 2013.
U.S. Appl. No. 12/357,239, Notice of Allowance.
U.S. Appl. No. 14/274,223, Non-Final Rejection, May 6, 2015.
U.S. Appl. No. 14/274,223, Final Rejection, Nov. 17, 2015.
U.S. Appl. No. 14/274,223, Advisory Action, Feb. 8, 2016.

METHODS AND DEVICES FOR INTRAORAL TACTILE FEEDBACK

CROSS-REFERENCE TO RELATED APPLICATIONS

This application is a continuation of U.S. application Ser. No. 14/274,223 filed May 9, 2014, which is a continuation of U.S. application Ser. No. 12/357,239 filed Jan. 21, 2009, which claims the benefit of U.S. provisional application No. 61/011,364 filed Jan. 17, 2008, the entire content of each of which is expressly incorporated herein by reference thereto.

FIELD OF TECHNOLOGY

The present invention relates to the field of articulation, speech, and language therapy. More particularly, the present invention relates to a method and device for interacting with the tongue in the oral cavity.

BACKGROUND

In order to produce the speech sounds that comprise the acoustic signal of human language, a complex set of coordinated muscle movements must be realized. Each speech sound requires that a unique series of movements be performed. For example, the tongue must change shape and/or make contact with various landmarks within the oral cavity, often in a precise sequence of movements. Many people, particularly children, may not be able to effect the particular series of movements necessary to produce a particular speech sound. For these individuals, the improper series of movements may result in distorted speech sounds that affect the overall intelligibility of their speech. The inability to produce commonly acceptable speech patterns in accordance with established norms within a community of speakers is known as an articulation disorder.

Traditional methods for treating articulation disorders use complex visual and verbal cues to indicate correct movement and placement of the oral articulators. However, speech sounds requiring proper tongue position, shape, and movement are difficult to teach because the required tongue position, shape, and movement take place behind the teeth and are difficult to show to a patient. As a result it is difficult for patients to assimilate these types of complex motor patterns when taught with traditional visual and verbal cues. In particular, complex verbal cues used to teach proper tongue shape and movement may be difficult for younger patients to process.

SUMMARY OF THE INVENTION

The present invention is directed to methods and devices for providing intraoral tactile feedback during articulation, speech, and language therapy/training. In accordance with one aspect of the invention, a speech articulation disorder may be treated by providing tactile feedback to the patient to indicate proper position of the tongue for the production of a target "sound". The term "sound" as used herein includes the phonetic terms phoneme and allophone. During treatment a patient will be able to discern proper production of a target sound through the tactile feedback provided when the target sound is properly produced. In order to provide tactile feedback for the proper production of a target sound, one or more nodes may be placed in the oral cavity of the patient in locations corresponding to the proper lingual position required to produce the target sound. The nodes may be specifically configured and arranged to cue the proper tongue position, shape, and/or movement required for various target sounds.

In accordance with another aspect of the invention, provided are devices for indicating the proper lingual position corresponding to particular speech sounds by providing intraoral tactile feedback. The devices may generally comprise one or more nodes and means for supporting and/or positioning the nodes inside the oral cavity. The nodes may take various shapes and sizes and may be specifically configured to cue the proper tongue position, shape, and/or movement required for specific target sounds. In some embodiments, the nodes can not only demonstrate static tongue positions, but also dynamic tongue movements. The means for supporting and/or positioning the nodes may take various configurations. However, the means for supporting and/or positioning the nodes are preferably configured so that the patient may navigate to and touch the nodes with his tongue with minimal physical impedance when producing the target sound. There are many possible embodiments for the means for supporting and/or positioning the nodes in the oral cavity, including handles, adhesives, harnesses supported on the teeth, harnesses supported on tissue, harnesses supported on external peripheral (such as headgear, eyewear), and mouth molds.

In order to treat or train various classes of consonant sounds in accordance with the methods and devices described herein, a therapist must be able to cue various tongue positions during the production of speech sound. To be able to cue the various tongue positions for the proper production of different speech sounds, a therapist may need to employ various node configurations to provide the proper tactile feedback. Thus, in accordance with another aspect of the invention, provided is a kit containing one or more devices for providing the proper tactile feedback for the production of a plurality of speech sounds.

Additional features and advantages of the invention will be made apparent from the following detailed description of illustrative embodiments that proceeds with reference to the accompanying drawings.

BRIEF DESCRIPTION OF THE DRAWING FIGURES

The foregoing summary, as well as the following detailed description of the preferred embodiments, is better understood when read in conjunction with the appended drawings. For the purpose of illustrating the invention, there are shown in the drawings embodiments that are presently preferred, it being understood, however, that the invention is not limited to the specific methods and instrumentalities disclosed. In the drawings:

FIG. 1 shows a flowchart of an exemplary implementation of a method for treating speech articulation disorders;

FIG. 2 shows a flowchart of an exemplary implementation of another method for treating speech articulation disorders FIG. 3 shows a flowchart of an exemplary implementation of another method for treating speech articulation disorders FIGS. 4A and 4B illustrate an exemplary placement of a series of targets in a patient's oral cavity to indicate the proper progression of tongue positions required to properly produce the /r/ sound;

DETAILED DESCRIPTION OF THE PREFERRED EMBODIMENTS

Figure 1:
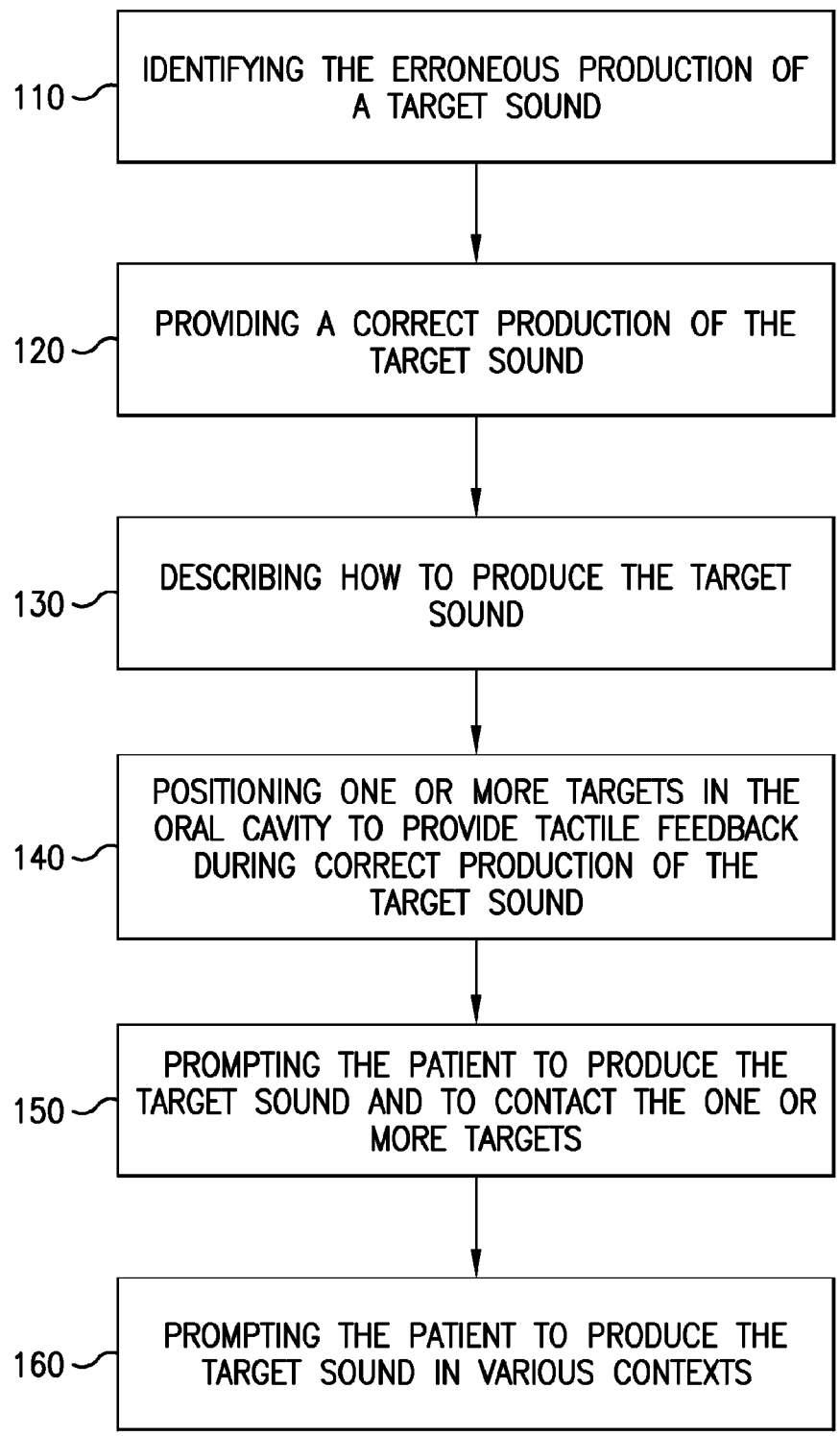

The successful production of any speech sound begins with adequate air capacity in the lungs. As air is expelled through the trachea, it generally vibrates the vocal folds within the human larynx, creating a vocalized speech sound. To produce the individual speech sounds, oral articulators within the oral cavity are manipulated by neuromuscular impulses. The primary oral articulator is the tongue. As the vocalized speech sound created in the larynx passes through the oral cavity, the oral articulators configure the oral cavity to produce a particular speech sound. Different oral configurations yield different speech sounds.

The present invention is directed to methods and devices for teaching the proper configuration of the oral articulators, particularly the tongue, corresponding to particular speech sounds by providing intraoral tactile feedback. Intraoral tactile feedback is achieved by placing nodes in the oral cavity for the tongue to contact while producing a particular speech sound. As used herein, the term node refers to a target that can be navigated to and touched by the tongue. These nodes will facilitate identification of the appropriate lingual position corresponding to a particular speech sound by providing tactilely differentiated targets for the tongue to contact. The proper positioning of the tongue indicated by tactile feedback combined with voiced or unvoiced vocalization will facilitate the proper production of a given sound.

The methods and devices may be particularly applicable for training correct production of consonant sounds. Further, the methods and devices may be particularly well suited for the training of speech sounds that are produced in areas of the mouth not visible to the speech pathologist or the patient. These speech sounds include, but are not limited to, /k/, /g/, /r/, /s/, /z/, /sh/, and /zh/.

In one embodiment, the invention relates to a method of treating a speech articulation disorder in a patient, which comprises providing a sound training device having one or more nodes to provide tactile feedback to the patient for the proper position of the tongue for a particular speech sound; and providing the device with registration features designed to position the device in a location in an oral cavity of a patient such that the patient's tongue is able to freely navigate to contact the one or more nodes to be positioned for making the particular sound; wherein the one or more nodes are configured and dimensioned to provide tactile feedback to the patient for the proper position of the tongue for the particular sound.

This method may further comprise positioning the one or more nodes in a location in the patient's oral cavity corresponding to the appropriate lingual position for a particular speech sound; and prompting the patient to make the particular speech sound by contacting the node or nodes with his or her tongue.

The preferred devices for use in accordance with the invention are selected from the group consisting of:

a first device comprising a cylindrical node configured to be positioned in a medial location inferior to the patient's palate to provide tactile feedback for the proper tongue position corresponding to the /r/ sound;

a second device comprising a node configured to be positioned in a location on the patient's alveolar ridge to provide tactile feedback for the proper tongue position corresponding to the /l/, /t/, or /d/ sound;

a third device comprising a pair of nodes configured to be positioned in lateral posterior locations on either side of the patient's palate to provide tactile feedback for the proper tongue position corresponding to the /k/ or /g/ sound;

a fourth device comprising a pair of nodes configured to be positioned in lateral anterior locations on either side of the patient's palate to provide tactile feedback for the proper tongue position corresponding to the /j/ (y) sound;

a fifth device comprising a node configured to be positioned in an anterior location inferior to the patient's palate to provide tactile feedback for the proper tongue position corresponding to the /s/, /z/, or /Σ/ (sh), or /Z/ (ζη) sounds; and a sixth device comprising a node configured to be positioned in an anterior location on the patient's palate to provide tactile feedback for the proper tongue position corresponding to the /τΣ/ (ch) or /δZ/ (j) sound.

The invention also relates to a method for making a device for treating a speech articulation disorder in a patient, which comprises preparing a sound training device with one or more nodes to provide tactile feedback to the patient for the proper position of the tongue for a particular speech sound; and preparing the device with registration features designed to position the device in a location in an oral cavity of a patient such that the patient's tongue is able to freely navigate to contact the one or more nodes to be positioned for making the particular sound; wherein the one or more nodes are configured and dimensioned to provide tactile feedback to the patient for the proper position of the tongue for the particular sound.

The devices made by the preceding method form yet another embodiment of the invention.

Another embodiment of the invention relates to a speech articulation disorder treatment article, comprising a sound training device that includes one or more nodes to provide tactile feedback for the proper tongue position corresponding to a particular speech sound, and registration features designed to position the target in a location in an oral cavity of a patient such that the patient's tongue is able to freely navigate to and contact the one or more nodes to be positioned for making the particular sound, wherein the nodes are configured and dimensioned to provide tactile feedback to the patient for the proper position of the tongue for the given sound.

This article preferably includes means for positioning the one or more nodes in a specific location in an oral cavity of the patient, the positioning means comprising a dental clip harness, an adhesive for attaching the target to the patient's mouth tissue or teeth, or a dental mold. Advantageously, the article includes a handle for holding and positioning the one or more nodes in the patient's oral cavity. The one or more nodes may be supported on a coil or a slide that allows the one or more nodes to move in response to pressure applied by the patient's tongue. The slides or coils can provide tactile as well as auditory information in the form of clicks or the like for providing feedback to the patient on tongue movement or tongue pressure on the nodes. The one or more nodes may also comprise a sensor for sensing lingual contact and transmitting a signal to a computer.

The nodes can be supported by the device in a number of ways. When a dental clip harness is used, it preferably comprises a dental clip for engaging a patient's tooth and a wire extending from the dental clip for supporting one or more nodes. In other embodiments, an adhesive can be used to directly affix the nodes to the patient's teeth or mouth tissue in the appropriate location. When a dental mold is used, the nodes can be integrally formed in or releasably attached to the dental mold. Alternatively, the nodes can be attached to or suspended from eyegear or headgear for assisting in placement in the patient's oral cavity.

In another embodiment, the nodes may be flavored or colored to add further cues (gustatory and visual cues, respectively) for the patient to associate his or her tongue in a correct position to speak a given sound. It is also possible to make the nodes of a soluble material to provide patients with a time frame for therapy sessions. The soluble material used may preferably be designed to dissolve gradually over the course of a therapy session.

The invention also relates to a kit for treating a speech articulation disorder in a patient, comprising a plurality of articles, each article comprising one or more sound training nodes to provide tactile feedback for the proper tongue position corresponding to a particular speech sound; and registration features designed to position the one or more nodes in a location in an oral cavity of a patient such that the patient's tongue is able to freely navigate to and contact the one or more nodes to be positioned for making the particular sound; wherein the one or more nodes of each article are configured to provide tactile feedback for the proper tongue position corresponding for a different sound.

In this kit, each article may be adapted to position the one or more nodes in a unique location in the patient's oral cavity which location corresponds to the proper position of the tongue for a proper sound. Two or more articles can be provided in the kit as desired. Each article in the kit can further comprise means for positioning the one or more nodes in a specific location in an oral cavity of the patient of the types disclosed herein. Each article in the kit may be associated with a respective handle, or a single handle can be provided for holding the specific target or nodes as desired for producing the desired sound.

And another embodiment of the invention relates to the use of one or more articles from the kits disclosed herein for treating a speech articulation disorder in a patient to teach proper positioning of a patient's tongue to properly pronounce various sounds. For example, one or more articles from the kit can be used for treating a speech articulation disorder in a hearing impaired person, in a person who suffers from acquired apraxia of speech, developmental apraxia of speech, or dysarthria or for training a person in a language that is foreign to his or her native language.

The methods and devices provide phoneme-specific articulatory facilitation with minimal physical impedance. More particularly, the methods and devices preferably allow unimpeded coarticulation (i.e. the natural transition of one speech sound or phoneme into another needed for forming words and sentences) while aiding in the exact lingual positioning required for accurate productions of specific speech sounds. This allows for smooth transitions in the therapy regimen and "natural" sounding speech while focusing on specific target sounds.

The methods and devices of the present invention may provide particular advantages in a number of specialized articulation, speech, and language treatment/training contexts. For example, the methods and devices of the present invention may be particularly useful in treating speech or articulation disorders in patients who are hearing impaired, have acquired apraxia of speech following stroke or other brain injury, have developmental apraxia of speech, or have dysarthria.

Articulation and phonological disorders are common among those with hearing impairment. Given this population's reduced capacity to process auditory and verbal cues in therapy, visual cues are emphasized. However, certain sounds are unfit for visual cuing (e.g. /s/, /z/, /Σ/ (sh), /Z/ (zh), /τΣ/ (ch), /δZ/ (j), /k/, and /g/) as the lingual movements crucial to production occur posterior to the teeth and cannot be fully visualized. Furthermore, the sibilant fricative consonants /s/, /z/, /Σ/ (sh), /Z/ (zh) are of high frequency (pitch) and are particularly difficult to perceive for those with hearing impairment. For these reasons, intra-oral tactile feedback may be particularly efficacious. For certain sounds, tactile cuing may be the only true cuing modality available to speech therapists for use with the hearing impaired.

Following a stroke or traumatic brain injury, a significant percentage of patients experience apraxia of speech (AOS). AOS represents a disruption of the patient's ability to select, sequence, and execute the necessary motor commands of a voluntary behavior such as speech. The patient often either cannot articulate certain speech sounds (e.g. /s/ or /sh/) or presents with pronounced difficulty in initiating speech. For many patients with AOS, the coordinated movement patterns required to produce certain speech sounds may be particularly difficult to select, sequence, and execute. Intra-oral tactile feedback may therefore be very helpful in providing a crucial tactile clue to the patient, with guided practice, to retrain the execution of necessary movements for the production of speech sounds.

As in acquired AOS, developmental AOS manifests as a disruption of the pediatric patient's ability to select, sequence, and execute the necessary motor commands of a voluntary behavior such as speech. However, patients with developmental AOS have difficulty with the complete articulatory gesture—from motor planning, to selection, to sequencing, and to final execution. Thus, therapy for developmental AOS may further emphasize a more step-by-step approach to training correct tongue placement. In addition, given the severity of the articulation disorder found in developmental AOS, intra-oral tactile feedback therapy may utilize a wide array of sound-specific devices. The redundancy of the articulation training using intra-oral tactile feedback (e.g. regimented, repetitive training) across related speech sounds (e.g. /s/ and /sh/) may provide an extra clinical benefit to patients diagnosed with developmental AOS.

Dysarthria is an acquired neurogenic communication disorder characterized by neuromuscular paralysis or weakness in the oral and facial musculature. Dysarthria can present secondary to a stroke or other brain injury, or as a result of a wide range of neurological impairments (e.g. Parkinson's disease, amyotrophic lateral sclerosis). Dysarthric speech is often described as weak and/or slurred, with a significant detrimental effect on a patient's overall intelligibility. Intra-oral tactile biofeedback may be particularly helpful in speech therapy with patients suffering from dysarthria. The weak, slurred speech patterns may be treated by placing tactile feedback nodes in the patient's oral cavity to provide targets that the patient may use during therapy sessions to identify landmarks associated with a given speech sound.

While the methods and devices may be particularly useful for speech articulation therapy, they may also be used for new language training (e.g. English as a Second Language (ESL), school-based or institute-based language instruction). For example, the methods and devices may be used to teach proper pronunciation for a language. Lingual location and patterns of movement at the time of phonemic execution vary in accordance with an individual's native language and dialect, and directly influence the production of phonemes in later-acquired languages. Thus, the methods and devices may be used to train proper lingual/palatal contact and lingual location for the consonants of a new language.

Additionally, the intra-oral tactile feedback devices and methods described herein may also be applied to non-English language speech sounds that are materially similar in place or manner of articulation. Other languages may include Chinese, Spanish, Hindi/Urdu, Arabic, Portuguese, Russian, Japanese, German, and French.

For example, the methods and devices described herein in connection with the English /t/ and /d/ sounds (alveolar stop consonants) may be used in connection with similar speech sounds in Chinese, Spanish, Hindi/Urdu, Arabic, Portuguese, Russian, Japanese, German and French.

The methods and devices described herein in connection with the English /l/ sound (an alveolar liquid consonant) may be used in connection with similar speech sounds in Chinese, Spanish, Hindi, Arabic, Portuguese, Russian, German, and French, but not Japanese.

The methods and devices described herein in connection with the English /τΣ/(ch) and /δZ/ (j) sounds (alveolar affricate consonants), may be used in connection with similar speech sounds in Chinese, Spanish (not /δZ/), Hindi/Urdu, Russian (not /δZ/), and German (not /δZ/), but not Arabic, Portuguese, or French.

The methods and devices described herein in connection with the English /s/ and /z/ sounds (alveolar sibilant fricative consonants) may be used in connection with similar speech sounds in Chinese (not /z/), Spanish, Hindi/Urdu, Arabic, Portuguese, Russian, Japanese, German, and French.

The methods and devices described herein in connection with the English /Σ/ (sh) and /Z/ (zh) sounds (post-alveolar sibilant fricative consonants) may be used in connection with similar speech sounds in Hindi/Urdu, Portuguese, Russian, German, and French, but not Chinese (correlate articulated more posteriorly), Spanish, Arabic, or Japanese.

The methods and devices described herein in connection with the English /g/ and /k/ sounds (velar stop consonants) may be used in connection with similar speech sounds in Chinese (not /g/), Spanish, Hindi/Urdu, Arabic (not /g/), Portuguese, Russian, Japanese, German, and French. In addition, though not present in English, German contains the velar fricative /x/. Intra-oral tactile biofeedback targeting the velar stop consonants /k/ and /g/ may also be applied to the velar fricative consonant /x/.

The methods and devices described herein in connection with the English /y/ and /j/ sounds (a palatal glide) may be used in connection with similar speech sounds in Chinese, Spanish, Hindi/Urdu, Arabic, Portuguese, Russian, Japanese, German, and French.

The methods and devices described herein in connection with the English /r/ sound (a retroflexed and/or retracted rhotic) may be used in connection with similar speech sounds in Chinese and Hindi/Urdu, but not Spanish, Arabic, Portuguese, Russian, Japanese, German, or French.

Methods

FIG. 1 shows a flowchart of one implementation of a method 100A for providing intra-oral feedback in speech training/therapy. The term "sound" as used herein includes the phonetic terms phoneme and allophone. In step 110, a therapist identifies the erroneous production of a sound ("target sound"). In step 120, the therapist provides a correct production of the target sound and an incorrect production of the error target sound and asks the patient to distinguish which is correct. In step 130, the therapist describes to the patient how to configure his tongue to properly create the target sound. In step 140, the therapist positions one or more targets or nodes in the patient's oral cavity to indicate the proper position of the tongue for producing the target sound through tactile feedback to the patient. In step 150, the therapist prompts the patient to produce the target sound and contact the target with his tongue. In step 160, the therapist prompts the patient to properly produce the target sound in various contexts. Step 160 preferably occurs after the patient is able to properly produce the target sound and serves to strengthen and stabilize the correct production of the target sound in all contexts.

The sequence of steps 110-160 in FIG. 1 is exemplary and is not intended to limit methods described herein to any particular sequence, nor is it intended to preclude adding steps, omitting steps, repeating steps, or performing steps simultaneously. For example, steps 120 may be repeated as deemed necessary by the therapist. The sequence of steps 130, 140, and 150 may be repeated as necessary until the patient properly produces the target sound. Additionally, the target may be adjusted as necessary in order to provide tactile feedback of the proper position of the tongue and achieve proper production of the target sound.

Figure 2:
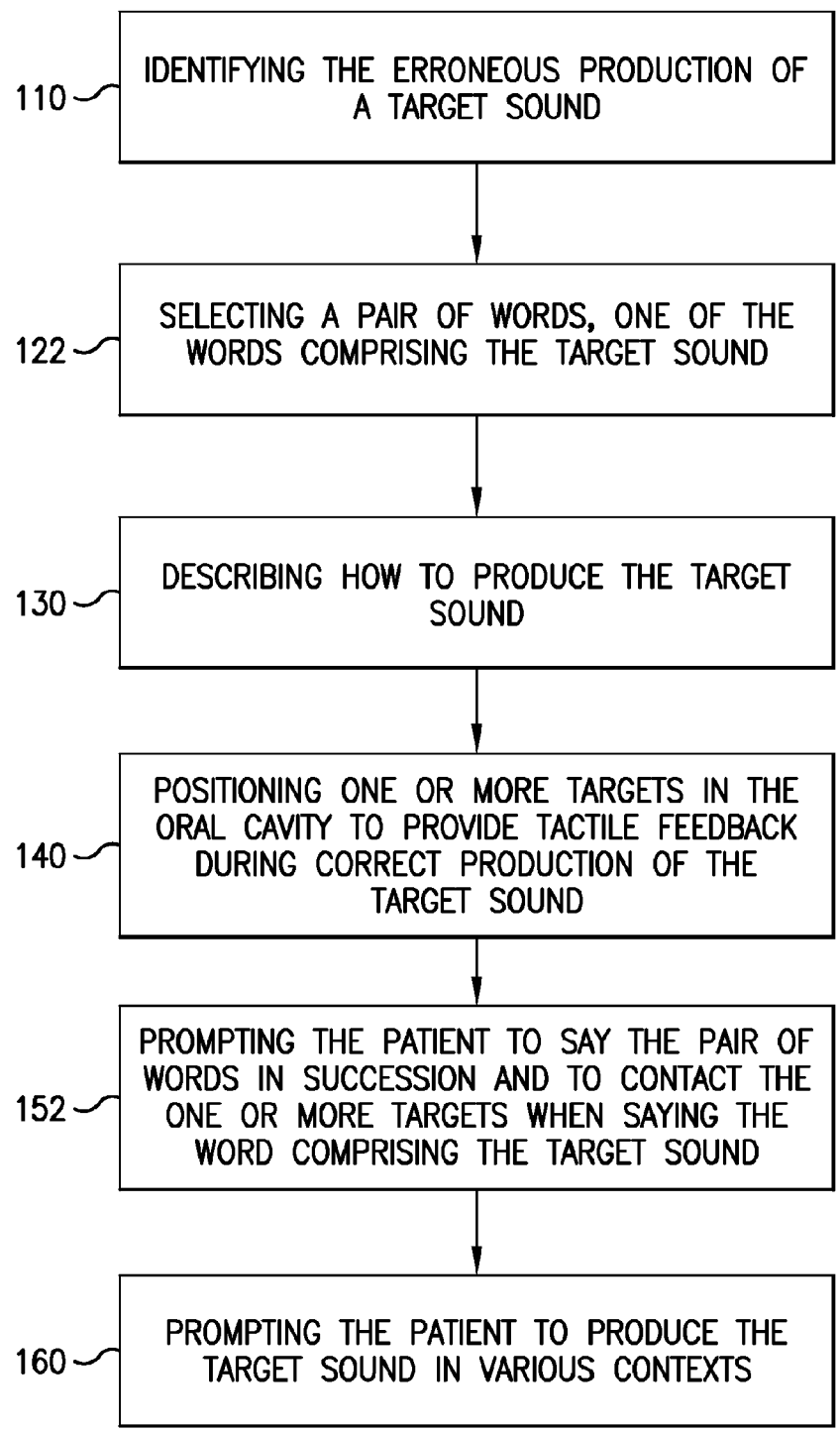

FIG. 2 shows another implementation of a method 100B for providing intra-oral feedback in speech training/therapy. In step 110, a therapist identifies the erroneous production of a sound ("target sound"). In step 122, the therapist selects a minimal pair of words that are identical except with respect to the target sound and a sound that the patient produces correctly. For example, if a patient incorrectly produces the /s/ sound and correctly produces the sound /t/, the therapist may select the pair of words /sip/ and /tip/. In step 130, the therapist describes to the patient how to configure his tongue to properly create the target sound. In step 140, the therapist positions one or more targets in the patient's oral cavity to indicate the proper position of the tongue for producing the target sound through tactile feedback to the patient. In step 152, the therapist prompts the patient to say the selected pair of words in succession and to contact the target with his tongue while saying the word containing the target sound. In step 160, the therapist prompts the patient to properly produce the target sound in various contexts. Step 160 preferably occurs after the patient is able to properly produce the sound and serves to strengthen and stabilize the correct production of the sound in all contexts.

The sequence of steps 110-160 in FIG. 2 is exemplary and is not intended to limit methods described herein to any particular sequence, nor is it intended to preclude adding steps, omitting steps, repeating steps, or performing steps simultaneously. For example, the sequence of steps 130, 140, and 152 may be repeated as necessary until the patient properly produces the target sound. Further, the sequence of steps 122, 130, 140, and 152 may be repeated by selecting another pair of words. Additionally, the target may be adjusted as necessary in order to provide tactile feedback of the proper position of the tongue and achieve proper production of the target sound.

The implementation of method 100B shown in FIG. 2 trains the patient to distinguish the target sound from a sound he already correctly produces by highlighting differences between the sounds in the selected pair of words. Intra-oral tactile feedback allows the patient to feel the difference between the sounds in the selected pair of words and enhances the contrast between correct and incorrect production of the target sound. This process allows the patient to train his somatosensory (i.e. higher level, innate feeling, and understanding of correct versus incorrect production of the target sound) and auditory systems to properly produce the target sound.

Figure 3:
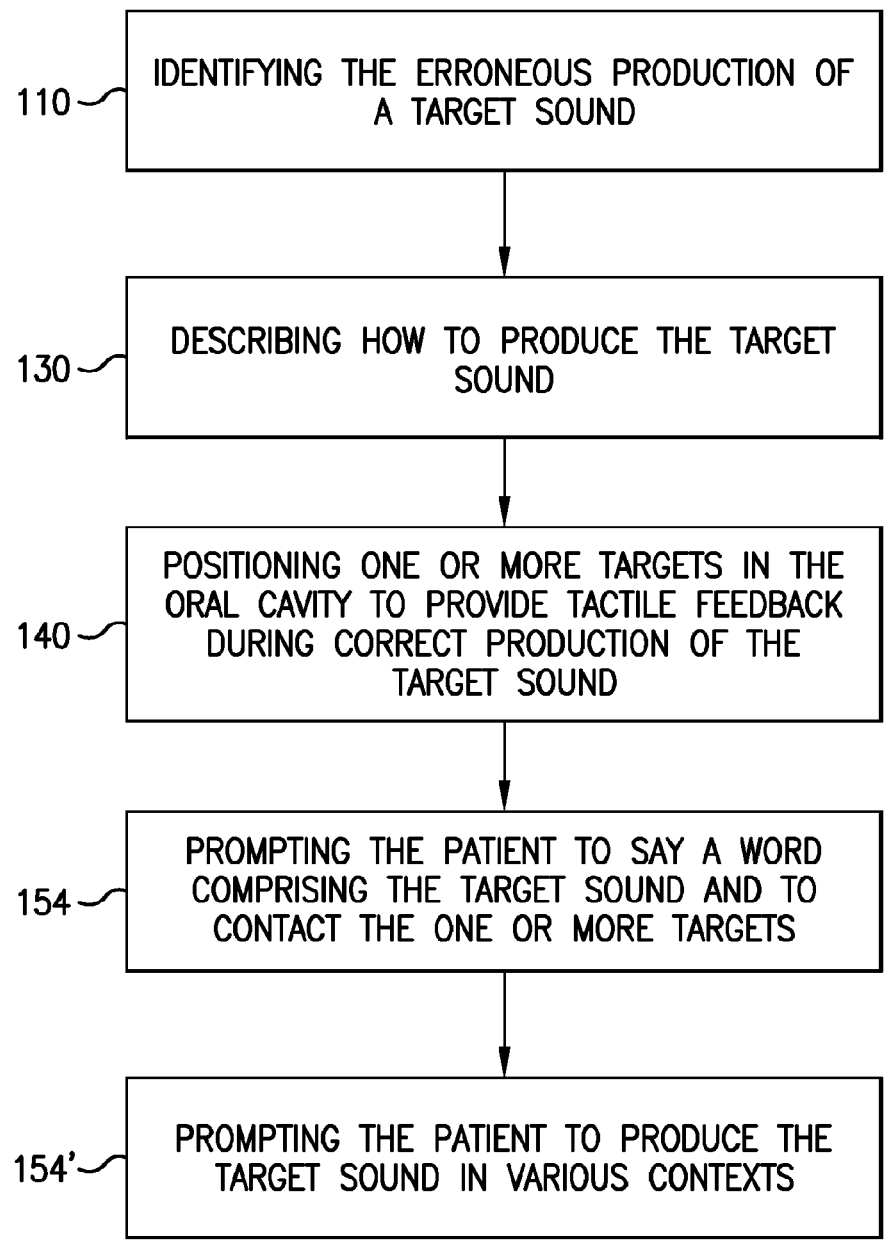

FIG. 3 shows a flowchart of another implementation of a method 100C for providing intra-oral feedback in speech training/therapy. In step 110, a therapist identifies the erroneous production of a sound ("target sound"). In step 130, the therapist describes to the patient how to configure his tongue to properly create the target sound. In step 140, the therapist positions one or more targets in the patient's oral cavity to indicate the proper position of the tongue for producing the target sound through tactile feedback to the patient. In step 154, the therapist prompts the patient to say a word containing the target sound and to contact the target with his tongue. Step 154 is preferably repeated with different words. This implementation of method 100C presents the patient with the target sound in many different co-articulatory contexts so that the patient is exposed to the target sound opposed with many other sounds. By presenting the target sound in many different contexts, the patient will more accurately perceive the target sound and will more accurately perceive how to reproduce the target sound. Providing intra-oral tactile feedback during repetitions of words containing the target sound allows the patient to better physically perceive accurate production of the target sound in various contexts.

The sequence of steps 110-154 in FIG. 3 is exemplary and is not intended to limit methods described herein to any particular sequence, nor is it intended to preclude adding steps, omitting steps, repeating steps, or performing steps simultaneously. For example, the sequence of steps 130, 140, and 154 may be repeated as necessary until the patient properly produces the target sound. Additionally, the target may be adjusted as necessary in order to provide tactile feedback of the proper position of the tongue and achieve proper production of the target sound.

Target Placement

In the methods described above, step 140 comprises positioning one or more targets in the patient's oral cavity to indicate the proper position of the tongue for producing the target sound through tactile feedback to the patient. Different sounds require different tongue positions. Thus, the target will have to be positioned in different locations in the oral cavity of the patient depending on the target sound being treated or trained. Below are some examples of target locations corresponding to the proper lingual position for the production of various speech sounds.

/r/ Phoneme Target Placement

Figure 4A:
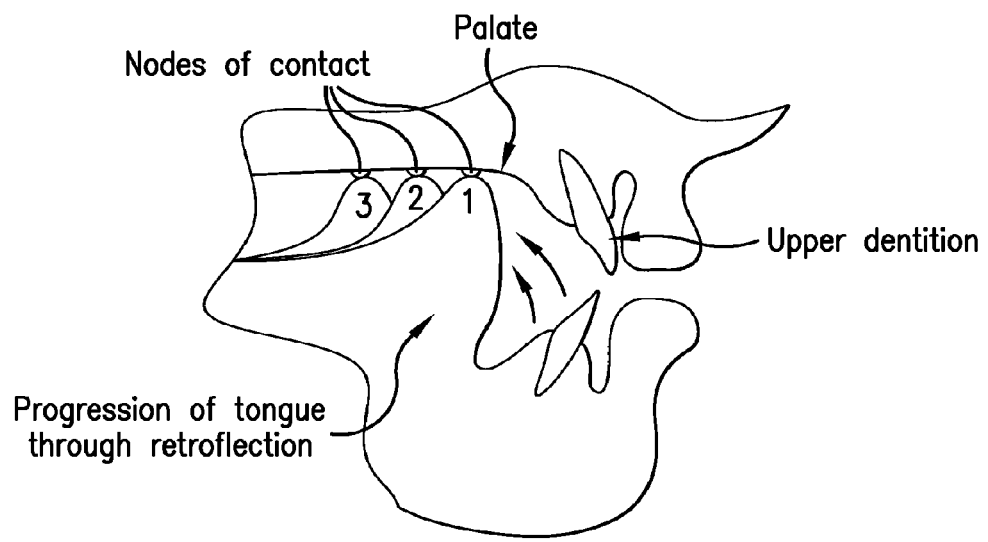
Figure 4B:
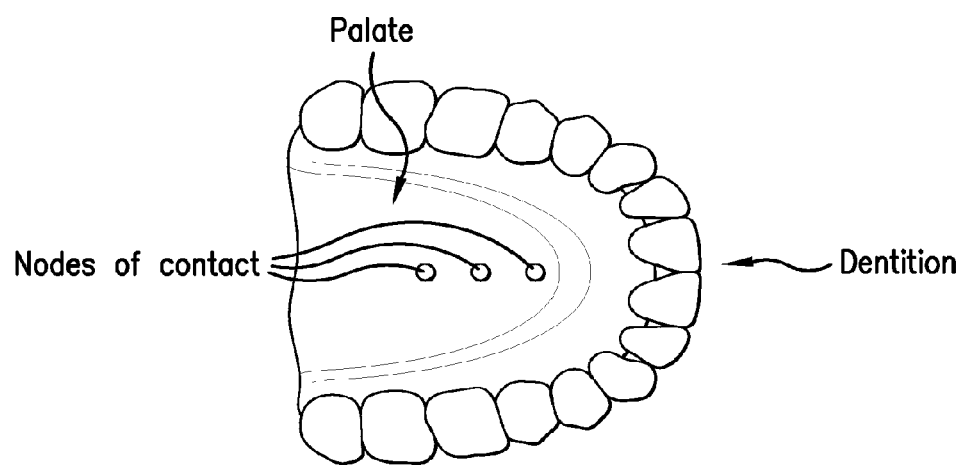

FIGS. 4A and 4B illustrate an exemplary placement of a series of targets in a patient's oral cavity to indicate the proper progression of tongue positions required to properly produce the /r/ sound. As shown in FIGS. 4A and 4B, a first target may be placed in a first medial anterior location below the palate. A second target may be placed in a second medial location posterior to the first location below the palate. And a third target may be placed in a third medial location posterior to the second location below the palate. Thus, these targets may provide tactile feedback when the tongue properly progresses through these three contact points to make the /r/ sound. The full progression of nodes presented in FIGS. 4A and 4B would generally corresponds to a patient who produces the /r/ sound using tongue retroflection (i.e. rolling the tongue posteriorly). However, the progression of nodes shown in FIGS. 4A and 4B may be modified to correspond to who produces the /r/ sound using tongue retraction (i.e. pulling the tongue slightly back and up).

/l/, /t/, and /d/ Phonemes Target Placement

Figure 5A:
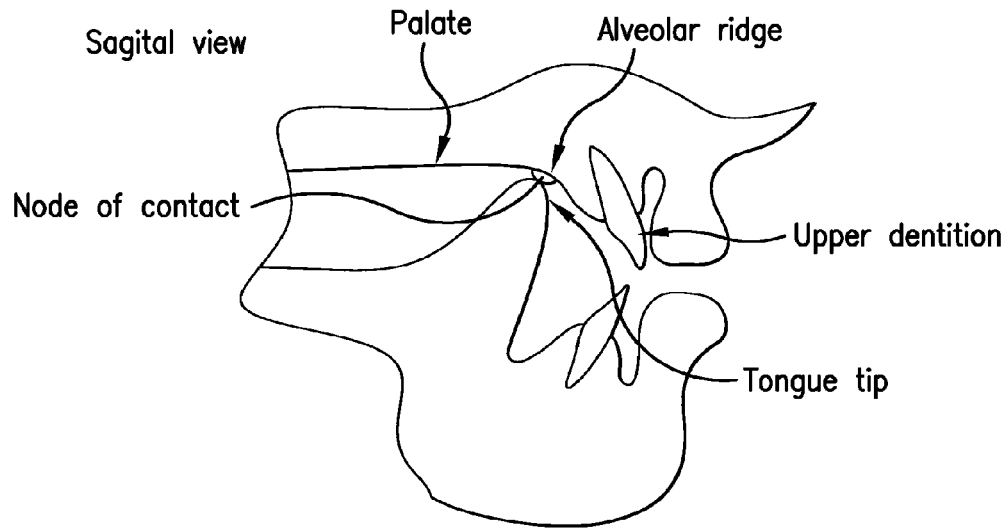
FIGS. 5A and 5B illustrate an exemplary placement of a target in a patient's oral cavity to indicate the proper tongue position required to properly produce the /l/, /t/, and /d/ sounds.
Figure 5B:
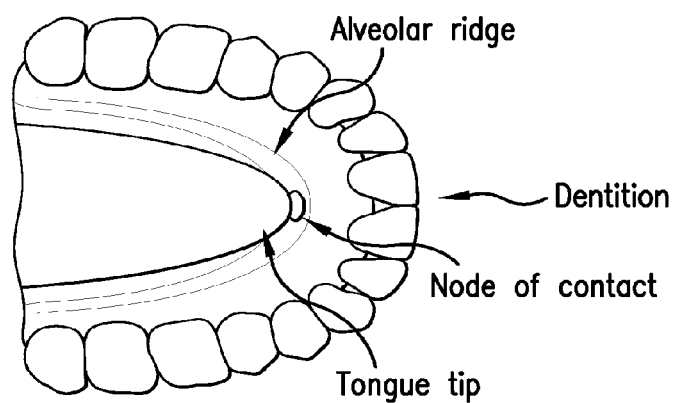

FIGS. 5A and 5B illustrate an exemplary placement of a target in a patient's oral cavity to indicate the proper tongue position required to properly produce the /l/, /t/, and /d/ sounds. As shown in FIGS. 5A and 5B, a target is preferably placed on the alveolar ridge in a medial location. Thus, the target may provide tactile feedback when the tongue is in the proper position to make the /l/, /t/, and /d/ sounds.

/k/ and /g/ Phonemes Target Placement

Figure 6A:
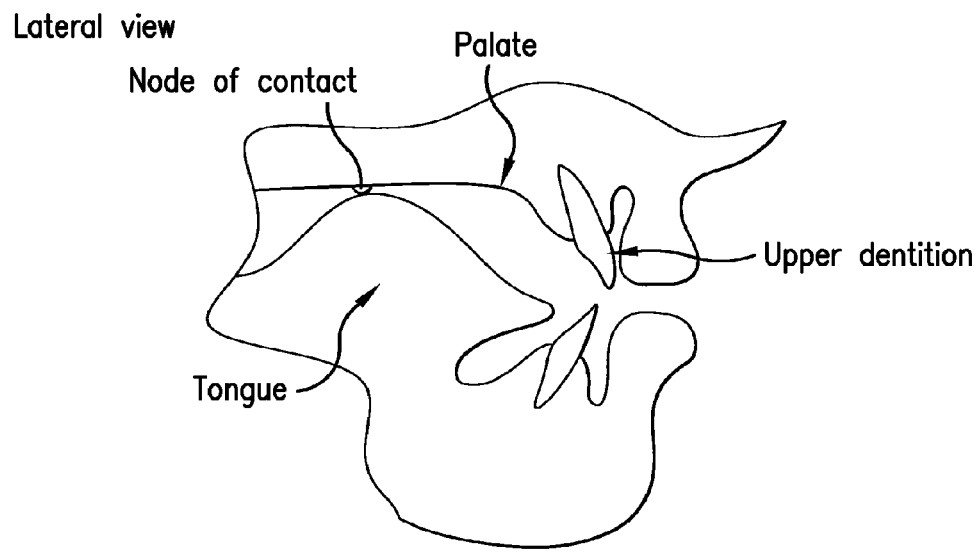
FIGS. 6A and 6B illustrate an exemplary placement of a pair of targets in a patient's oral cavity to indicate the proper tongue position required to properly produce the /k/ and /g/ sounds.
Figure 6B:
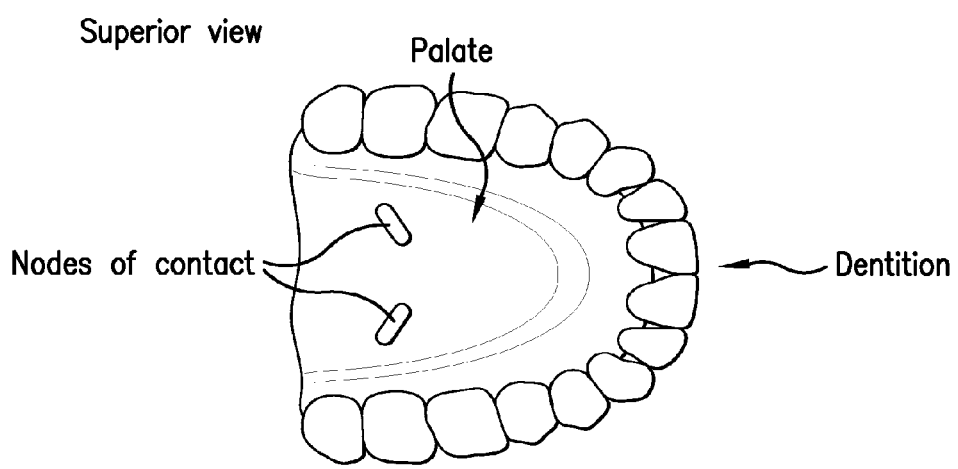

FIGS. 6A and 6B illustrate an exemplary placement of a pair of targets in a patient's oral cavity to indicate the proper tongue position required to properly produce the /k/ and /g/ sounds. As shown in FIGS. 6A and 6B, two targets are preferably placed on the palate in lateral posterior locations on either side of the palate. Thus, the targets may provide tactile feedback when the tongue is in the proper position to make the /k/ and /g/ sounds.

/s/, /z/, /Σ/ (sh), and /Z/(ζη) Phonemes Target Placement

Figure 7A:
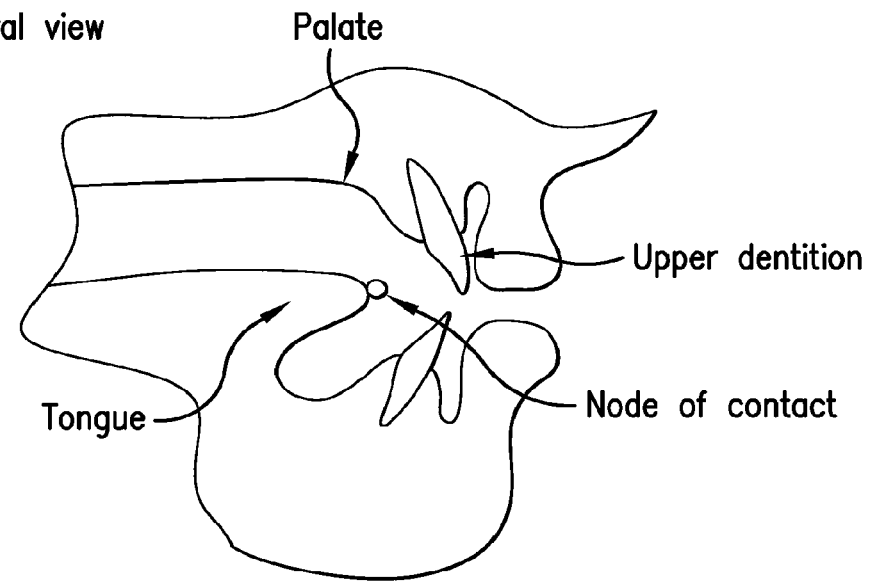
FIGS. 7A and 7B illustrate an exemplary placement of a target in a patient's oral cavity to indicate the proper tongue position required to properly produce the /s/ and /z/ sounds.
Figure 7B:
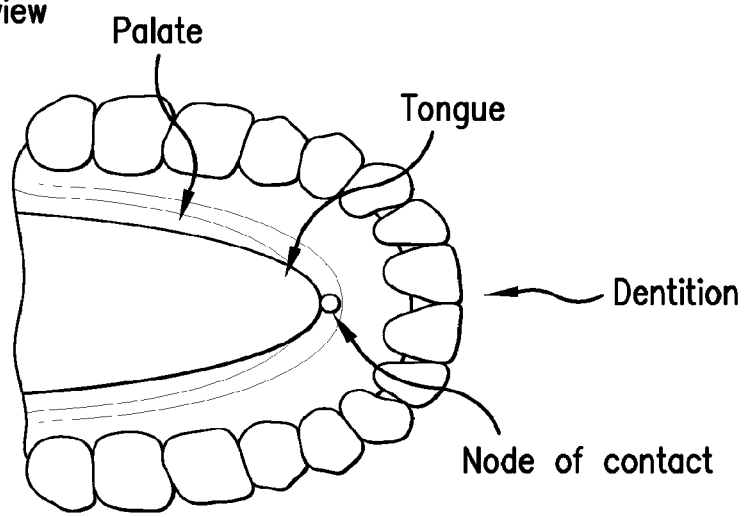

FIGS. 7A and 7B illustrate an exemplary placement of a target in a patient's oral cavity to indicate the proper tongue position required to properly produce the /s/, /z/, /Σ/ (sh), and /Z/ (ζη) sounds. As shown in FIGS. 7A and 7B, a target is preferably placed in a medial location below the alveolar ridge. Thus, the target may provide tactile feedback when the tongue is in the proper position to make the /s/, /z/, /Σ/ (sh), and /Z/ (ζη) sounds.

/τΣ/ (ch) and /δZ/ (j) Phonemes Target Placement

Figure 8A:
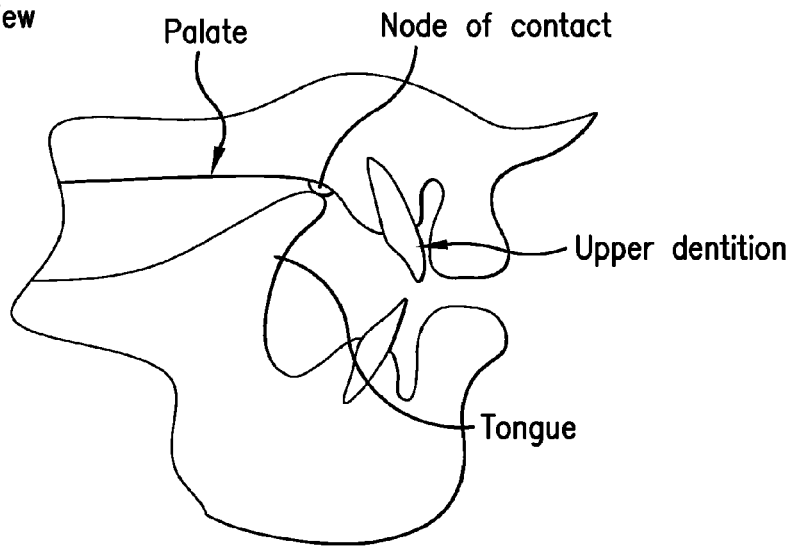
FIGS. 8A and 8B illustrate an exemplary placement of a target in a patient's oral cavity to indicate the proper tongue position required to properly produce the /τΣ/ (ch) and /δZ/ (j) sounds.
Figure 8B:
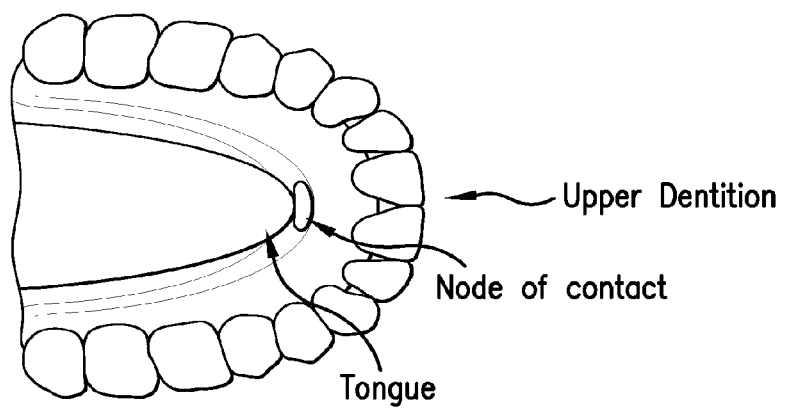

FIGS. 8A and 8B illustrate an exemplary placement of a target in a patient's oral cavity to indicate the proper tongue position required to properly produce the /τΣ/ (ch) and /δZ/ (j) sounds. As shown in FIGS. 8A and 8B, a target is preferably placed on the palate in a medial anterior location. Thus, the target may provide tactile feedback when the tongue is in the proper position to make the /τΣ/ (ch) and /δZ/ (j) sounds.

/j/ (y) Phoneme Target Placement

Figure 9A:
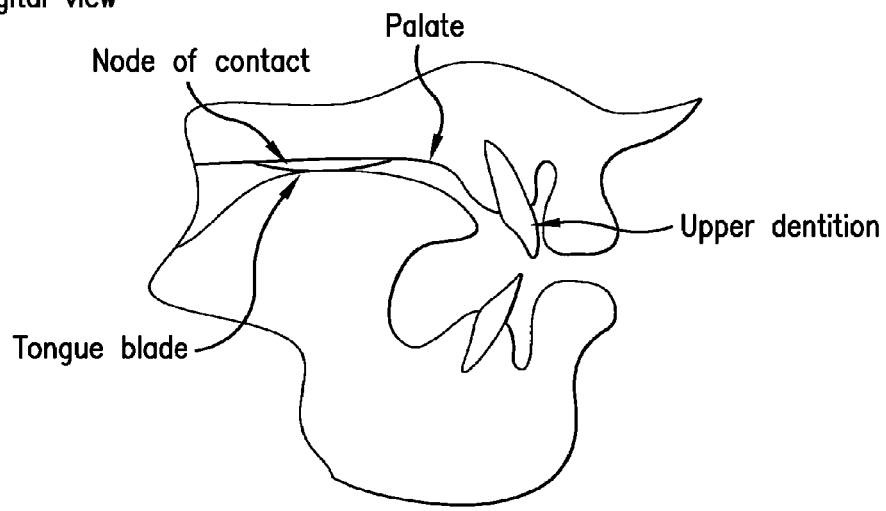
FIGS. 9A and 9B illustrate an exemplary placement of a pair of targets in a patient's oral cavity to indicate the proper tongue position required to properly produce the /j/ (y) sound.
Figure 9B:
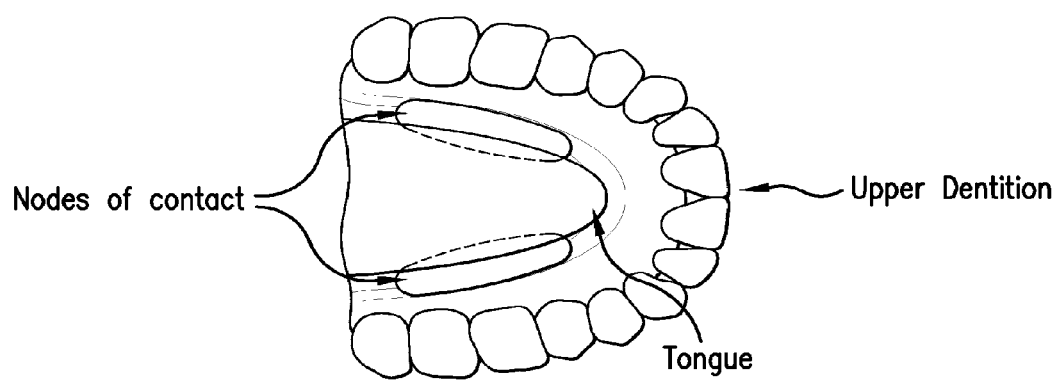

FIGS. 9A and 9B illustrate an exemplary placement of a pair of targets in a patient's oral cavity to indicate the proper tongue position required to properly produce the /j/ (y) sound. As shown in FIGS. 9A and 9B, two targets are preferably placed on the palate in lateral anterior locations on either side of the palate. Thus, the targets may provide tactile feedback when the tongue is in the proper position to make the /j/ (y) sound.

Node Placement for Elimination of Tongue Protrusion

Figure 10:
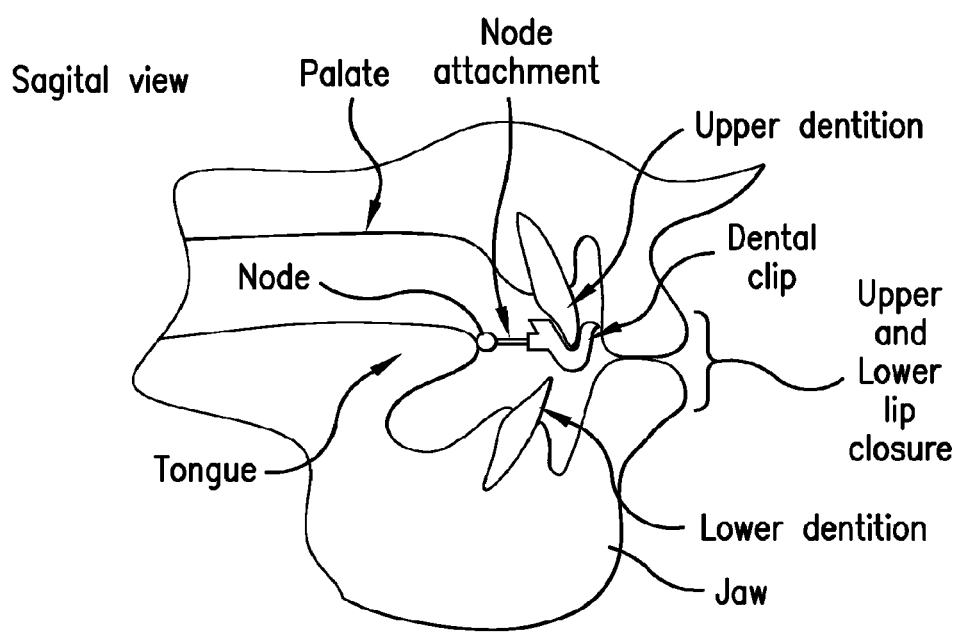
FIG. 10 illustrates an exemplary placement of a node to prevent protrusion of the tongue to properly produce speech sounds.
Figure 11A:
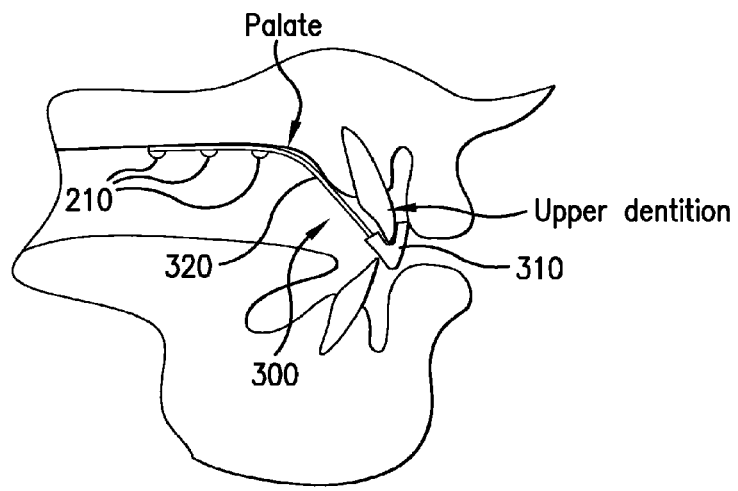
FIGS. 11A, 11B, 11C and 11D show an exemplary embodiment of a dental clip harness device.
Figure 11B:
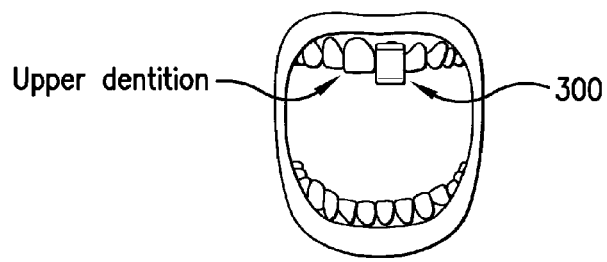
Figure 11C:
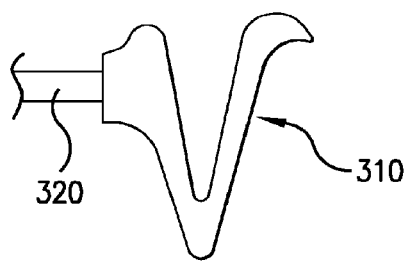
Figure 11D:
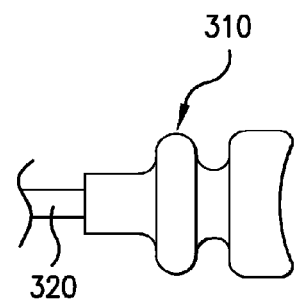

This implementation is designed to counter the problem of tongue thrust, where a patient protrudes their tongue between the lips during efforts to generate speech. This behavior distorts many speech sounds (including vowels as well as consonant sounds) because the tongue becomes misaligned for all speech sound production and because the lips cannot seal. This behavior is generally seen among, though not limited to, people who have Down Syndrome, epilepsy, cerebral palsy, or who have had strokes or other brain injury. FIG. 10 illustrates an exemplary placement of a node to prevent protrusion of the tongue to properly produce speech sounds. As shown, a node may be placed either on the alveolar ridge or just below the alveolar ridge to prevent the tongue from thrusting through their lips.

Devices

In accordance with another aspect of the invention, provided are devices 200 for indicating the proper lingual position corresponding to particular speech sounds by providing intraoral tactile feedback. While devices 200 are particularly applicable to the methods of treatment/training described above, they may also be applicable to other methods of treatment not described herein. Devices 200 are preferably minimally invasive and sympathetic to the contours of the oral cavity to allow unimpeded coarticulation (the natural transition of one speech sound or phoneme into another needed for forming words and sentences) while aiding in the exact lingual positioning required for accurate productions of specific speech sounds. These features allow smooth transitions during a therapy regimen and "natural" sounding speech while focusing on specific speech sounds.

Generally, devices 200 comprise one or more nodes 210 and means 220 for supporting and/or positioning the nodes 210. The nodes 210 may take various shapes and sizes. Nodes 210 can range in size from very small contact points to large contact pads. Nodes 210 can be comprised of, but not limited to: solid substrates, compliant substances or springs, dissolvable substrates, sharp contact points, contact points with a particular taste, contacts providing an electrical pulse, textured films, or any combinations thereof. The means 220 for supporting and/or positioning the nodes 210 are preferably configured so that the nodes 210 may be positioned inside the oral cavity of the patient and so that the patient may navigate to and touch the nodes 210 with his tongue with minimal physical impedance. Devices 200 can be made of a range of materials, including plastics (ABS, polycarbonate, polystyrene, peek, silicone, etc.), metals (stainless steel, titanium etc.) s, or combination of materials. These materials may be disposable or reusable. Thus, the entire device 200 may be designed as a disposable or re-usable device or specific components may be designed as disposable or reusable components.

In embodiments comprising dissolvable substances, nodes 210 may be flavored. Further, different nodes 210 corresponding to different speech sounds may be flavored differently to provide specificity to the feedback cues for distinguishing speech sounds. Also, nodes 210 could be colored in keeping with their flavor (e.g., purple for blackcurrant, orange for orange), hence adding further cues for the patient to associate with a given sound before device 200 is placed in their mouth. Additionally, the soluble nature of nodes 210 in this embodiment provides patients with a time frame for therapy sessions, as they would conclude a therapy exercise when the node is consumed. Such temporal incentives are advantageous when working with children or with the cognitively impaired, who may lose patience with a given activity. Such patients also frequently require multi modal cues (as provided by this embodiment—flavor, color, tactile, auditory, and visual) to during treatment.

Specific embodiments of nodes 210 may be adapted to enable phoneme-specific articulatory facilitation. For example, nodes 210 may be adapted to train tongue position, movement, and shape corresponding to proper production of a specific speech sound. Further, nodes 210 can not only demonstrate static tongue positions, but also dynamic tongue movements. For example, a series of nodes 210 can be arranged to provide successive tactile cues to help achieve a desired tongue movement. The series of nodes 210 may be provided in a single device or in a series of devices. Specific embodiments of nodes 210 adapted for phoneme-specific articulatory facilitation are discussed in detail below with reference to the figures.

In accordance with a further aspect of the invention, the nodes 210 may comprise electrode sensors (not shown) that serve to interface devices 200 with a computer. The computer may comprise software that monitors tongue contact with the node 210 and provides, among other things, real-time on-screen visualization of lingual contacts with nodes, "game" style positive reinforcement based on progress, data collection and statistical analysis, play back of recorded verbal reproductions as an indication of the status of patient speech productions, and comprehensive array of pre-recorded model phoneme productions to encourage greater accuracy via imitation. Such interactive programs may be interfaced with hardware via Universal Serial Bus (USB) or wireless units. Integrating multi-sensory information or cues during therapy may enhance the overall learning experience.

There are many possible embodiments for the means 220 for supporting and/or positioning the nodes 210 in the oral cavity, including handles, adhesives, harnesses supported on the teeth, harnesses supported on tissue, harnesses supported on external peripheral (such as headgear, eyewear), and mouth molds. Further, mechanical attachment of devices 200 to the teeth and/or the tissue in the mouth may be accomplished through various means, including spring force, tension, friction, microtextures, hydrophilic gradient, or other suitable means. The various embodiments of the means 220 for supporting and/or positioning the nodes 210 may be custom fit to the mouth of a specific patient, may be one size fits all, or may cover the range of human anatomy through various sizes.

Exemplary embodiments of devices 200 having different means 220 for supporting and/or positioning different node 210 configurations are described below with reference to the Figures. Although the devices 200 may be shown and described in connection with specific embodiments of means 220 and nodes 210, it should be understood that the following device 200 embodiments are only exemplary and are not intended to define or limit the invention. In addition to the device 200 embodiments shown, other device 200 embodiments comprising different combinations of means 220 and nodes 210 are contemplated by the inventors.

Dental Clip Harness

FIG. 11 shows an exemplary embodiment of a device 200 having support means 220 comprising a dental clip harness 300. In this embodiment, device 200 is clipped onto the teeth to support and position node 210 in the oral cavity. Means 220 for supporting and/or positioning nodes 210 comprise a dental clip 310 and a wire 320 extending from the dental clip 310. One or more nodes 210 may be disposed on one or more wires 320. Nodes 210 may be particularly configured and particularly positioned on one or more wires 320 according to the particular speech sound being treated, as described in connection with the target placement of the methods above. The placement of the series of nodes 210 shown in FIG. 11 corresponds to the production of the /r/ sound, but the device 200 shown in FIG. 11 may be configured for the treatment of any sound.

Dental Adhesive Harness

Figure 12A:
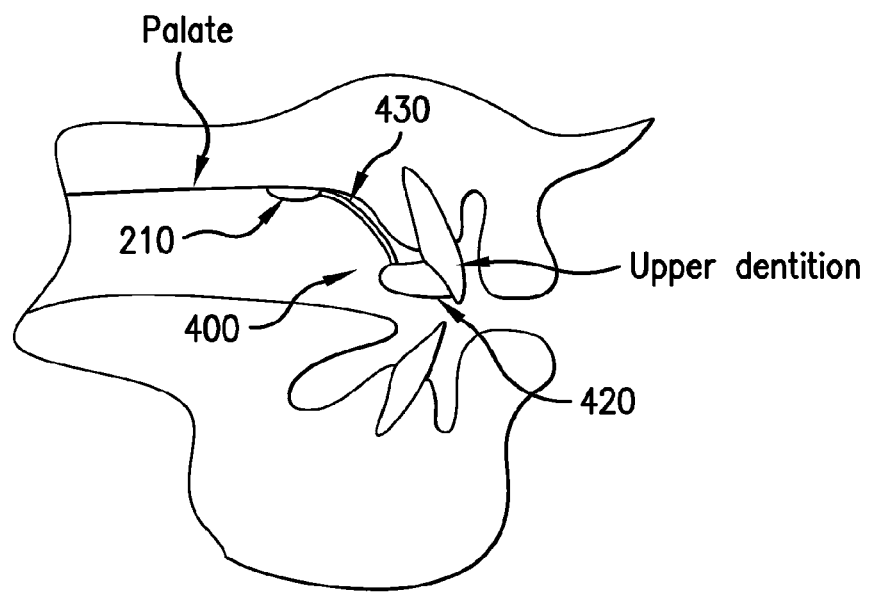
FIGS. 12A and 12B show an exemplary embodiment of a dental adhesive harness device.
Figure 12B:
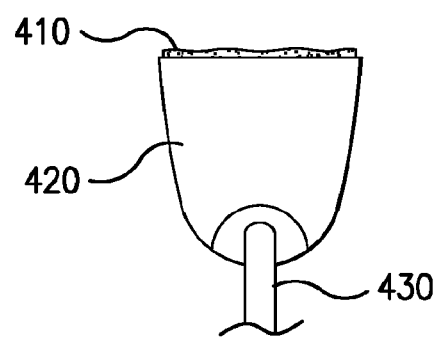

FIG. 12 shows an exemplary embodiment of a device 200 having support means 220 comprising a dental adhesive harness 400. In this embodiment, to support and position node 210 in the oral cavity, device 200 is affixed to the teeth using an adhesive 410. Means 220 for supporting and/or positioning node 210 comprise a base 420 affixed to the teeth with an adhesive 410, and a wire 430 extending from the base 420. One or more nodes 210 may be disposed on one or more wires 430. Nodes 210 may be particularly configured and particularly positioned on one or more wires 430 according to the particular speech sound being treated, as described in connection with the target placement of the methods above. The placement of node 210 shown in FIG. 12 corresponds to the production of the /tƩ/ (ch) and /ðZ/ (j) sounds, but the device 200 shown in FIG. 12 may be configured for the treatment of any sound. Adhesive 410 can produce a firmer grounding than the clip 310, which may be useful in working with young children or cognitively disordered patients who might seek to unduly remove device 200.

Tissue Adhesive Harness

Figure 13A:
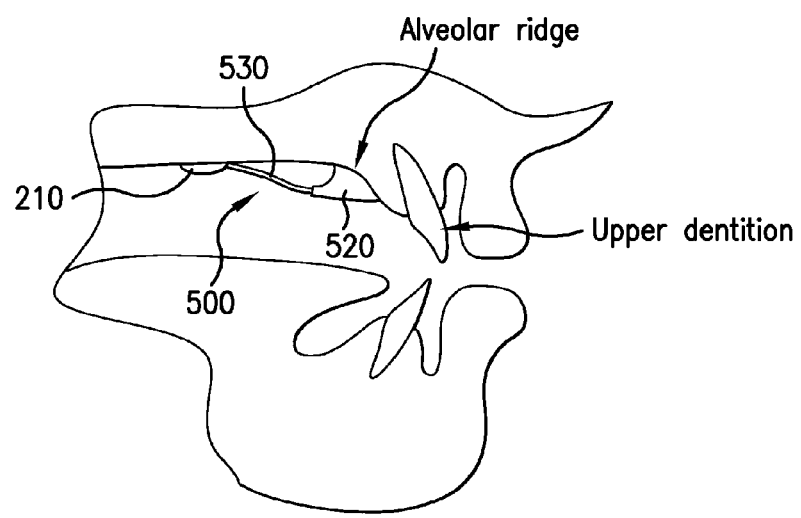
FIGS. 13A, 13B and 13C show an exemplary embodiment of a tissue adhesive harness device.
Figure 13B:
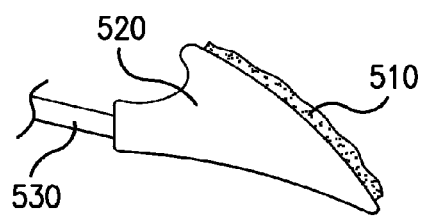
Figure 13C:
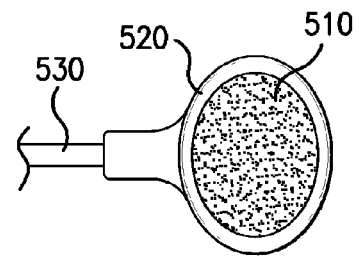

FIG. 13 shows an exemplary embodiment of a device 200 having support means 220 comprising a tissue adhesive harness 500. In this embodiment, to support and position node 210 in the oral cavity, device 200 is affixed to tissue in the oral cavity using an adhesive 510. Means 220 for supporting and/or positioning the nodes 210 comprise a base 520 affixed to the tissue of the oral cavity with an adhesive 510, and a wire 530 extending from the base 520. One or more nodes 210 may be disposed on one or more wires 530. Nodes 210 may be particularly configured and particularly positioned on one or more wires 530 according to the particular speech sound being treated, as described in connection with the target placement of the methods above. The placement of nodes 210 shown in FIG. 13 corresponds to the production of the /j/ (y) sound, but the device 200 shown in FIG. 13 may be configured for the treatment of any sound. This embodiment eliminates the necessity of dentition in the patient, which allows children in the process of losing their teeth, patients who have lost their dentition, or patients with atypical dental/facial structures to use device 200.

Independent Adhesive Node/Node Array

Figure 14A:
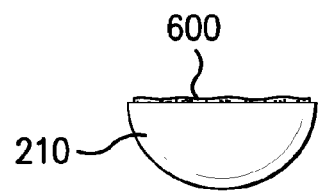
FIGS. 14A, 14B and 14C show an exemplary embodiment of an independent adhesive node/node array.
Figure 14B:
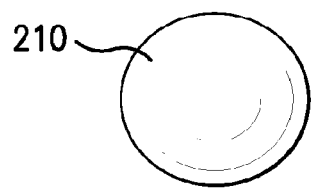
Figure 14C:
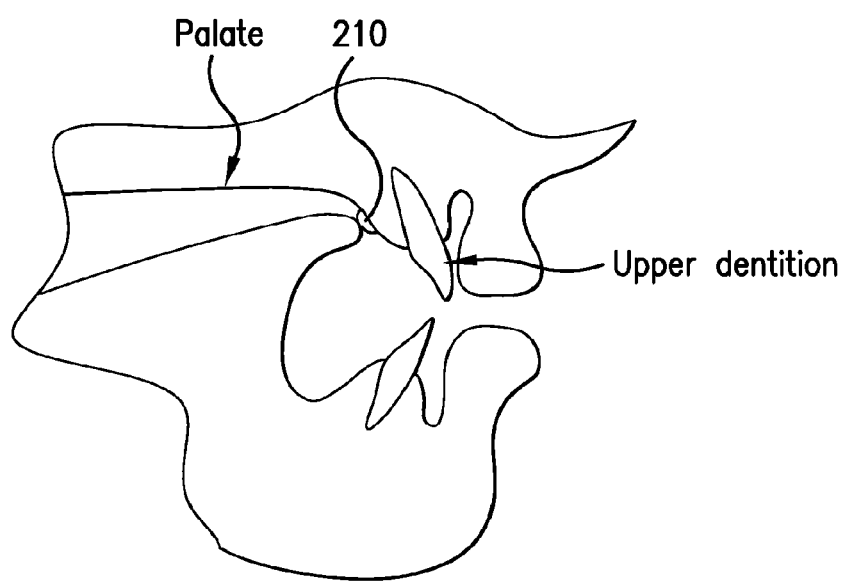

In the embodiment shown in FIG. 14, node 210 is affixed directly to the tissue of the oral cavity. Means 220 for supporting and/or positioning node 210 comprise an adhesive 600. Nodes 210 may be particularly positioned in the oral cavity according to the particular speech sound being treated, as described in connection with the target placement of the methods above. The placement of nodes 210 shown in FIG. 14 corresponds to the production of the /t/ and /d/ sounds, but the device 200 shown in FIG. 14 may be configured for the treatment of any sound.

Figure 15A:
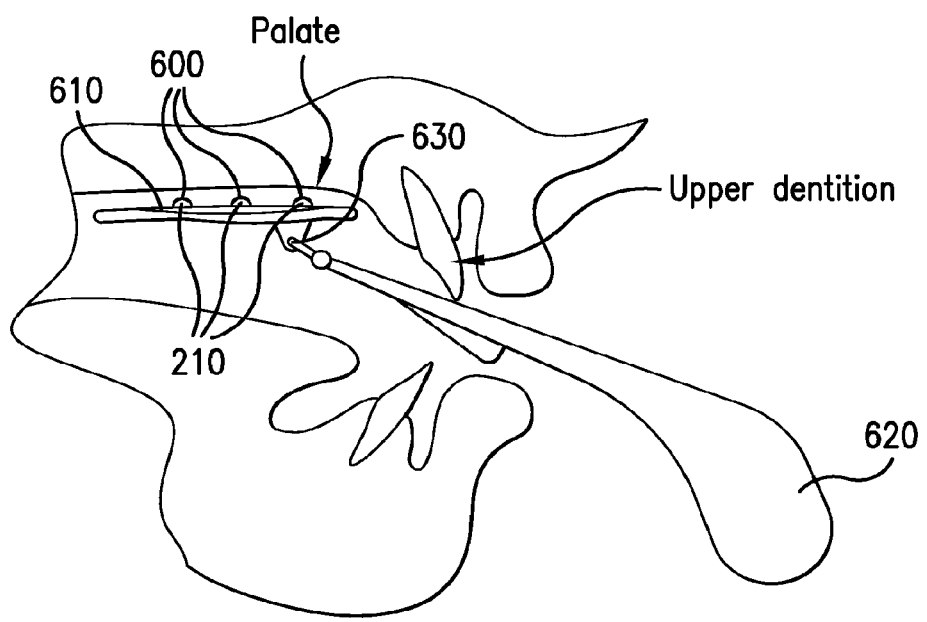
FIGS. 15A and 15B show an exemplary embodiment of plate for placing nodes in an oral cavity.
Figure 15B:
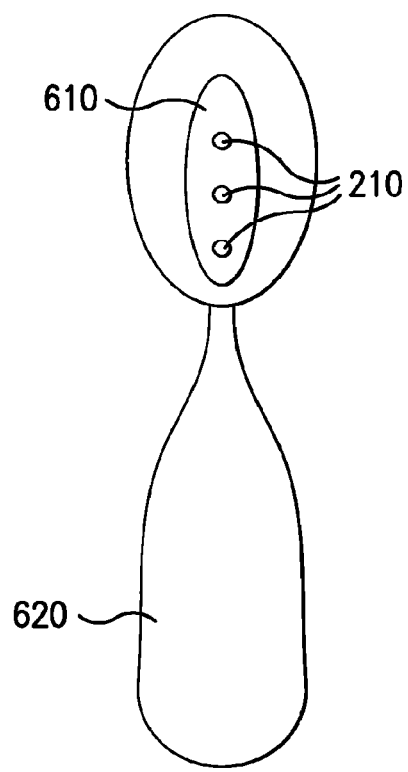

In this embodiment, nodes 210 could be arranged on a plate 610 attached to a handle 620 (as shown in FIG. 15) for accurate and efficient placement of nodes 210 in the patient's oral cavity. Handle 620 may be connected to plate 610 by a hinge 630, such as a ball and socket hinge, that allows plate 610 to move with respect to handle 610. After proper positioning of nodes 210 on the plate 610 and application of adhesive to nodes 210, nodes 210 may be placed inside the oral cavity and affixed to tissue by manipulating handle 620. This embodiment ensures reliable and consistent placement of nodes 210 in the oral cavity, thereby facilitating consistent production of speech sounds.

Dental Mold

Figure 16A:
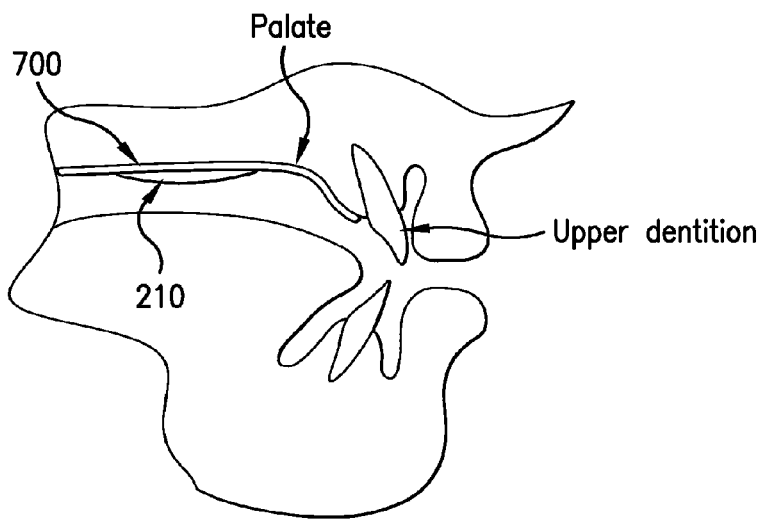
FIGS. 16A and 16B show an exemplary embodiment of a dental mold device.
Figure 16B:
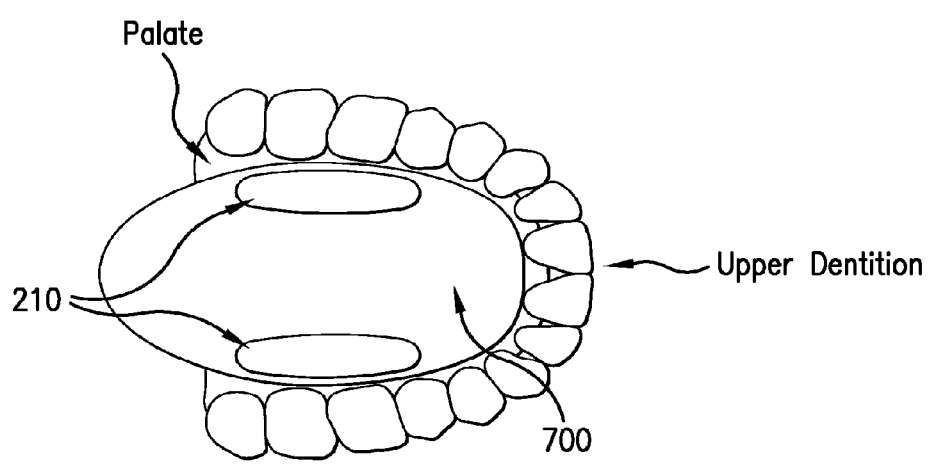

FIG. 16 shows an exemplary embodiment of a device 200 comprising a dental mold 700. In this embodiment, means 220 for supporting and/or positioning nodes 210 comprise a dental mold 700 which can be retained in the oral cavity. One or more nodes 210 may be disposed on dental mold 700 and may be integrally formed with dental mold 700 or removably attached to dental mold 700. Nodes 210 may be particularly positioned on dental mold 700 according to the particular speech sound being treated, as described in connection with the target placement of the methods above. The placement of nodes 210 shown in FIG. 16 corresponds to the production of the /j/ (y) sound, but the device 200 shown in FIG. 16 may be configured for the treatment of any sound. Dental molds 700 may be manufactured in several pre-established sizes to accommodate a broad range of oral cavity sizes or may be custom tailored for a patient.

Articushades/Articuglasses/Articugoggles

Figure 17A:
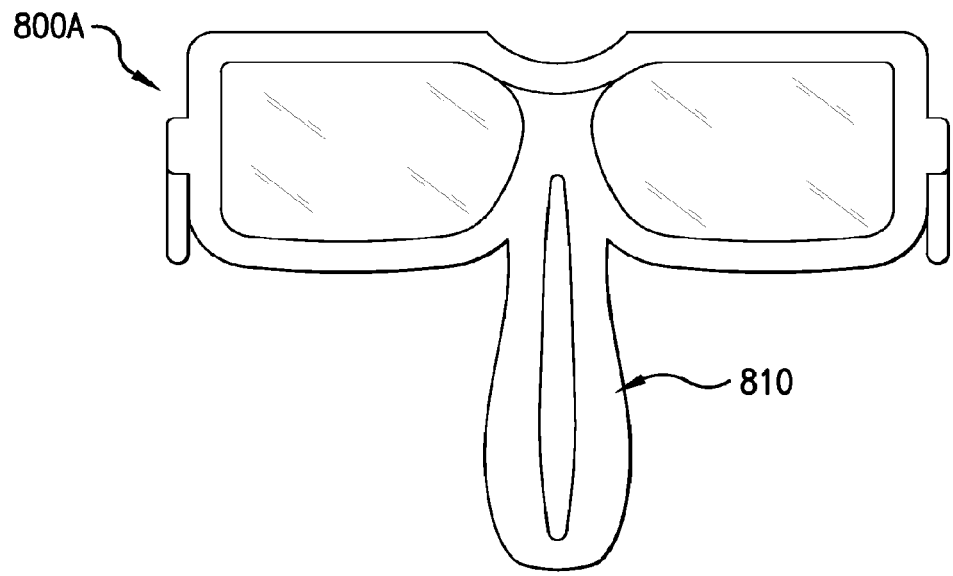
FIGS. 17A, 17B, 17C and 17D show an exemplary embodiment of an eyewear/headgear device.
Figure 17B:
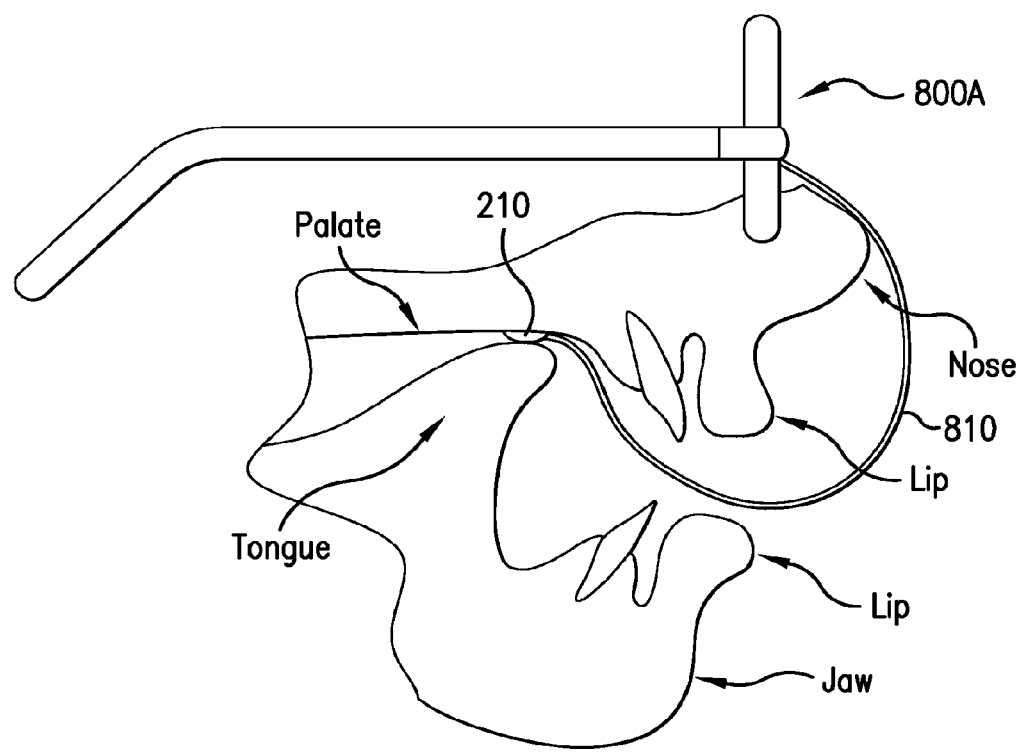
Figure 17C:
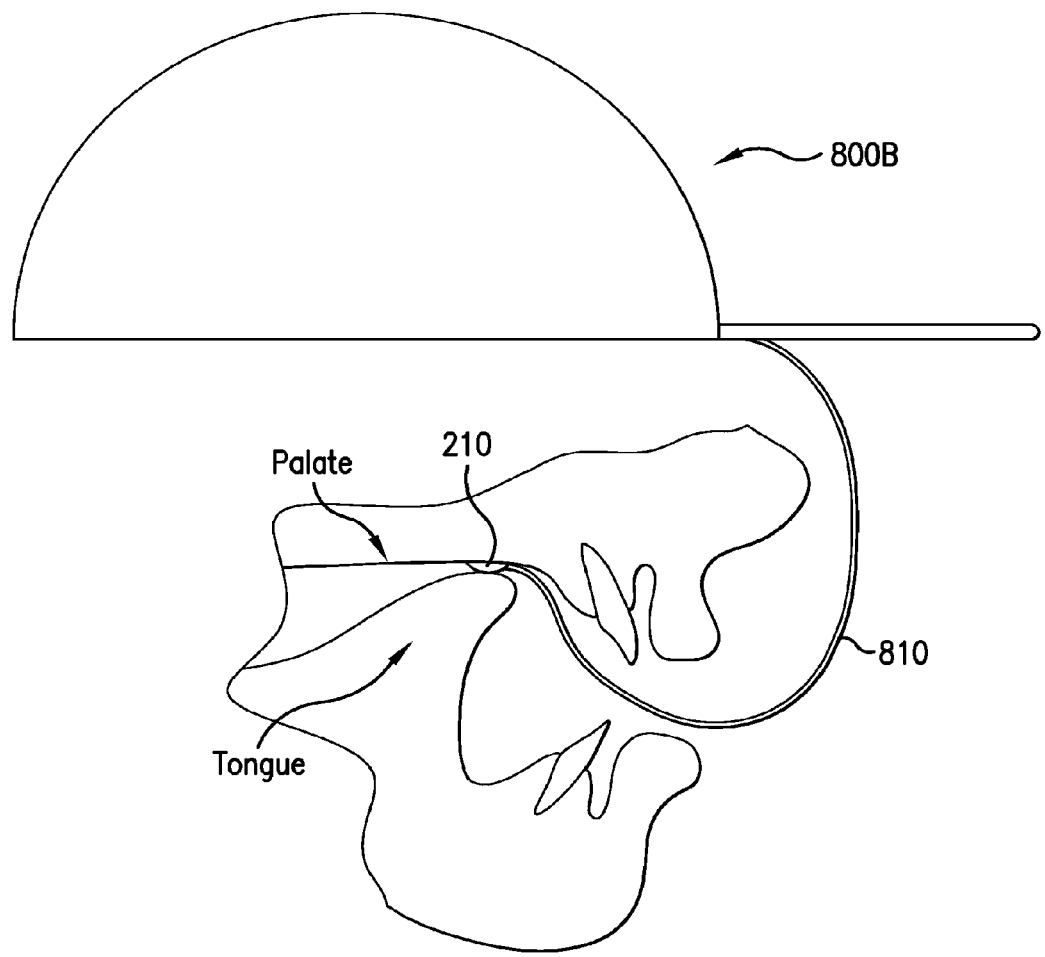
Figure 17D:
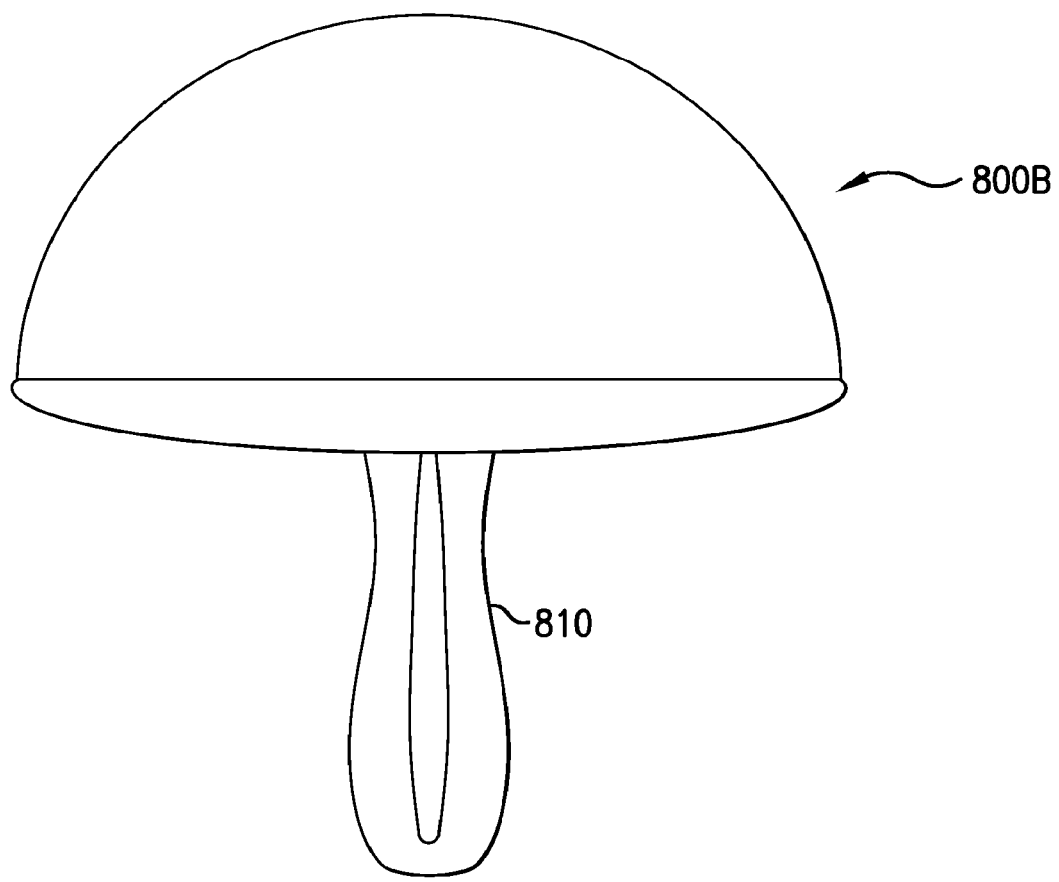

FIGS. 17A and 17B show exemplary embodiments of devices 200 having support means 220 comprising eyewear 800A or headgear 800B. In these embodiments, means 220 for supporting and/or positioning nodes 210 comprise either eyewear 800A or headgear 800B. One or more supports 810 may be attached to eyewear 800A or headgear 800B and one or more nodes 210 may be disposed on one or more supports 810. Nodes 210 may be particularly configured and particularly positioned on one or more supports 810 according to the particular speech sound being treated, as described in connection with the target placement of the methods above. The placement of node 210 shown in FIGS. 17A and 17B corresponds to the production of the /τΣ/ (ch) and /δZ/ (j) sounds, but the device 200 shown in FIGS. 17A and 17B may be configured for the treatment of any sound.

Film Platform

Figure 18A:
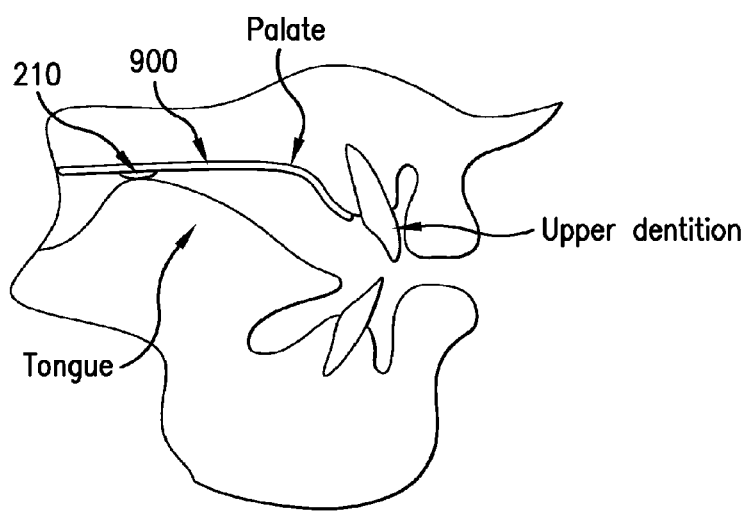
FIGS. 18A and 18B show an exemplary embodiment of a film device.
Figure 18B:
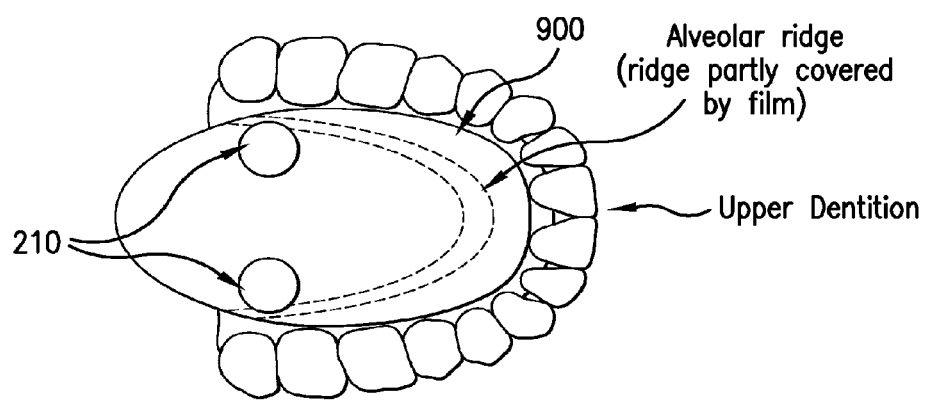

FIG. 18 shows an exemplary embodiment of a device 200 comprising a film 900. In this embodiment, means 220 for supporting and/or positioning nodes 210 comprise a film 900 which can be retained in the oral cavity. One or more nodes 210 may be disposed on film 900 and may be integrally formed with film 900. Nodes 210 may be particularly positioned on dental mold 700 according to the particular speech sound being treated, as described in connection with the target placement of the methods above. The placement of nodes 210 shown in FIG. 18 corresponds to the production of the /k/ and /g/ sounds, but the device 200 shown in FIG. 18 may be configured for the treatment of any sound. Film 900 is preferably pre-mapped with nodes 210 in appropriate locations to facilitate the production of specific speech sounds. Film 900 may be disposable or film 900 and nodes 210 may be integrally formed of a material that dissolves in the patient's mouth. Using dissolvable materials facilitates a timeline for therapy sessions and eliminates the need to retrieve device 200 from the oral cavity. Further, nodes 210 could be flavored to increase multimodal sensory awareness.

/r/ Progression Slide

Figure 19A:
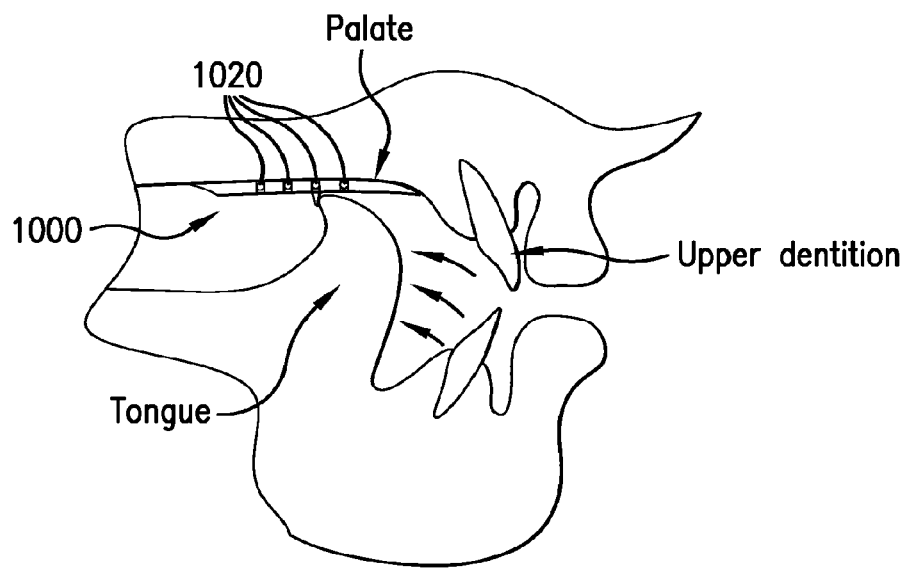
FIGS. 19A and 19B show an exemplary embodiment of a spring slide platform device.
Figure 19B:
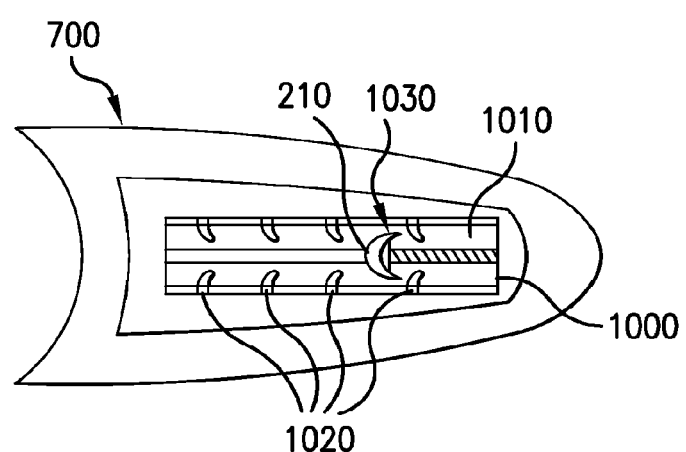

FIG. 19 shows an exemplary embodiment of a device 200 comprising a slide platform 1000. In this embodiment, means 220 for supporting and/or positioning node 210 comprise a slide platform 1000 which can be retained in the oral cavity. Slide platform 1000 preferably has an elongate shape and comprises a channel 1010 that defines a plurality of gates 1020 aligned along a longitudinal axis. Further, platform 1000 comprises a clip 1030 that is slidably disposed in channel 1010 and is adapted to click through gates 1020.

Slide platform 1000 may be retained in the oral cavity by attaching it to either a mold 700 or a clip 310 or attaching it directly to tissue in the oral cavity using adhesives. In this embodiment, node 210 is disposed a spring slide platform 100 so that when tongue pressure is applied superiorly and posteriorly on node 210, node 210 progresses posteriorly, by either tongue retroflection or tongue retraction, along the spring slide platform 1000 clicking through the gates 1020 to indicate progress. Sliding node 210 posteriorly with the tongue tip while vocalizing may facilitate the production of the /r/ speech sound. The concept of "clicks" may be used to mark stages of tongue progression, to provide patients with benchmarks, and to provide indications of progress toward the goal of generating the /r/ sound.

/y/ Shelf

Figure 20A:
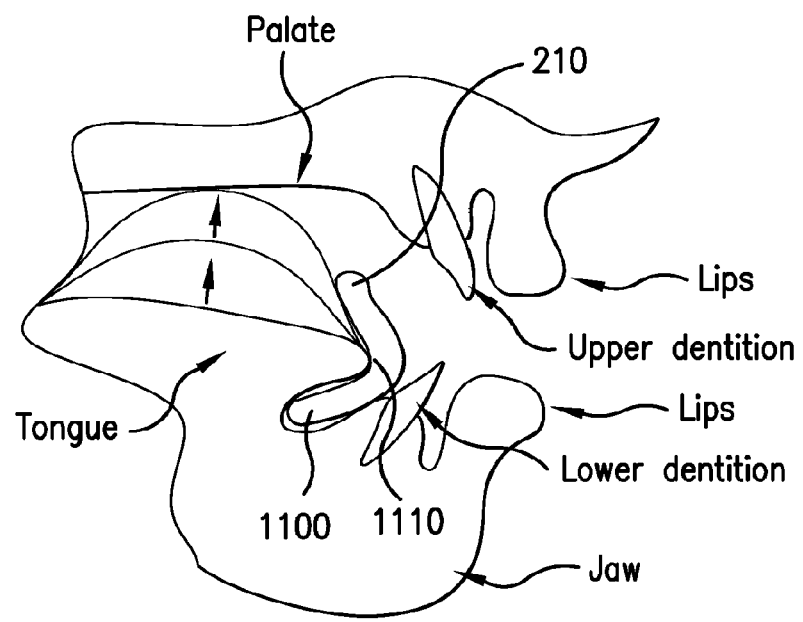
FIGS. 20A and 20B show an exemplary embodiment of a /y/ shelf device.
Figure 20B:
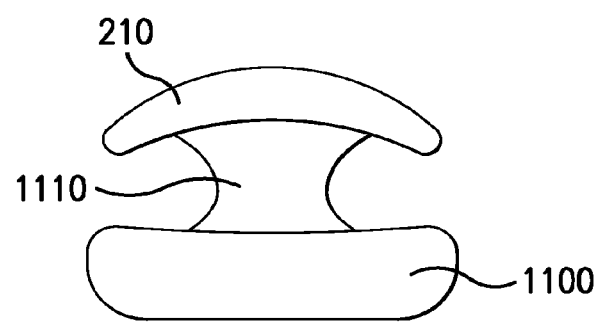

In correct production of the /y/ sound, the tongue blade (middle portion of the tongue just posterior to the tongue tip) rises toward the palate. FIG. 20 shows an exemplary embodiment of a device 200 comprising a base 1100 adapted to facilitate proper production of the /y/ sound. In this embodiment, means 220 for supporting and/or positioning node 210 comprise a base 1100 which can be retained in the oral cavity and a transition portion 1110 extending upwardly from contoured base 1100. Base 1100 is contoured to fit in inferior anterior oral cavity, posterior to the inferior dentition, and anterior to the tongue. Transition portion 1110 extends upwardly from base 1100 and supports node 210 on its superior end. Transition portion preferably has a concave shape to provide a trap for the tip of the tongue. Node 210 is preferably configured to define a shelf on the superior end of transition portion 1110. Thus, as the patient produces the /y/ sound, node 210 catches the tip of the tongue and causes the blade of the tongue to rise toward the palate, resulting in proper production of the /y/ sound.

/r/ Coil Attachment

Figure 21:
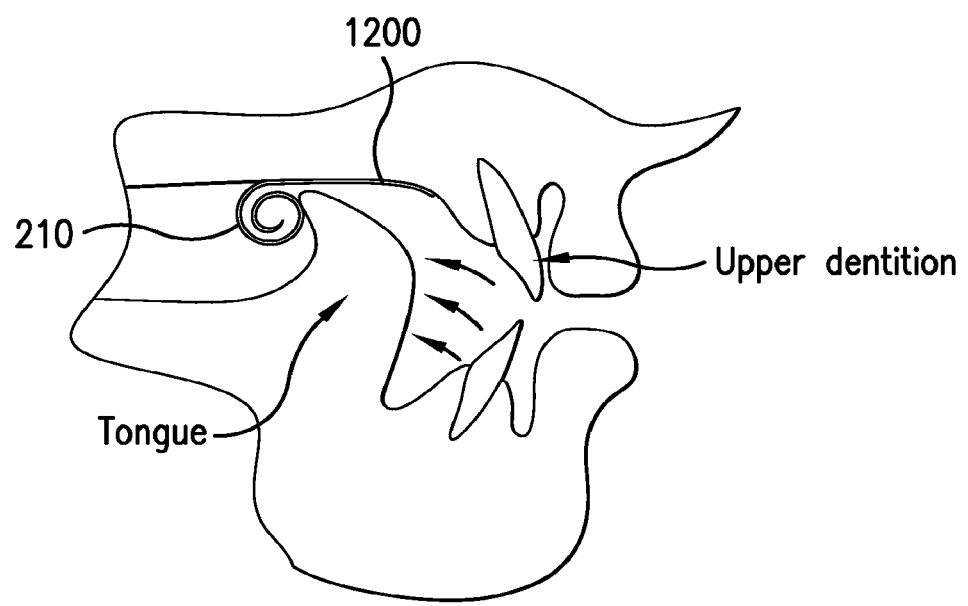
FIG. 21 shows an exemplary embodiment of an /r/ coil attachment.

The /r/ sound is a difficult sound to produce because it involves a progressive superior and posterior movement of the tongue just below the hard palate. FIG. 21 shows an exemplary embodiment of an attachment 1200 adapted to facilitate proper production of the /r/ sound, whether the patient generally produces /r/ with tongue retroflection or tongue retraction. In this embodiment, means 220 for supporting and/or positioning node 210 comprise an attachment 1200 that is adapted to be attached to a device platform, such as those device platforms described in this application (e.g. dental mold, handle, etc.), or directly to the palate with adhesives. Node 210 is supported on attachment 1200 such that node 210 may be disposed below the palate to cue the progression of the tongue along a path that generates the /r/ sound. In this embodiment, node 210 is configured in a coil shape that is resistant enough to require pressure from the tongue to uncoil in a posterior direction. In order to properly produce the/r/sound, a patient may contact the coil node 210 with their tongue tip and vocalize while unraveling the coil by moving the tongue tip posteriorly.

Handle-Based Devices

FIGS. 22-31 show various embodiments of devices 200 comprising a handle 1300. In these embodiments, means 220 for supporting and/or positioning node 210 may comprise a handle 1300 and a node support 1310 connected to and extending from handle 1300. One or more nodes 210 may be disposed on the end of node support 1310. Nodes 210 are configured on device 200 so that nodes 210 may be inserted into the oral cavity and positioned to indicate the proper tongue position for a given sound. Nodes 210 may be configured on devices 200 in accordance with the target placement for the methods described above. Thus, once positioned in the oral cavity at a location corresponding to the proper tongue position for a given sound, nodes 210 can provide tactile feedback for proper production of that sound.

Handle 1300 allows manipulation of the position and orientation of nodes 210 in the oral cavity. Handle 1300 preferably has a rectangular cross section so that the orientation of the device 200 may be easily determined, but may be any other suitable shape that allows easy determination of the orientation of device 200 (e.g. oval, ellipse). Also, handle 1300 is preferably long enough to allow the therapist's hands to remain at a comfortable distance for the patient so that device 200 may be manipulated unobtrusively. More particularly, handle 1300 may preferably be adapted to keep the therapist's hands as far away from the patient's mouth as possible, while still close enough to enable precise movements of device 200 within the patient's oral cavity. In a preferred embodiment, handle 1300 is 115 mm long.

Figure 22A:
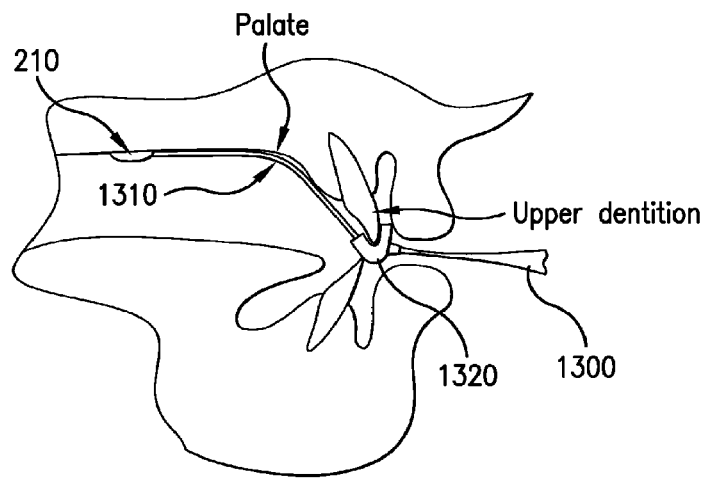
FIGS. 22A and 22B show an exemplary embodiment of a handle-based device.
Figure 22B:
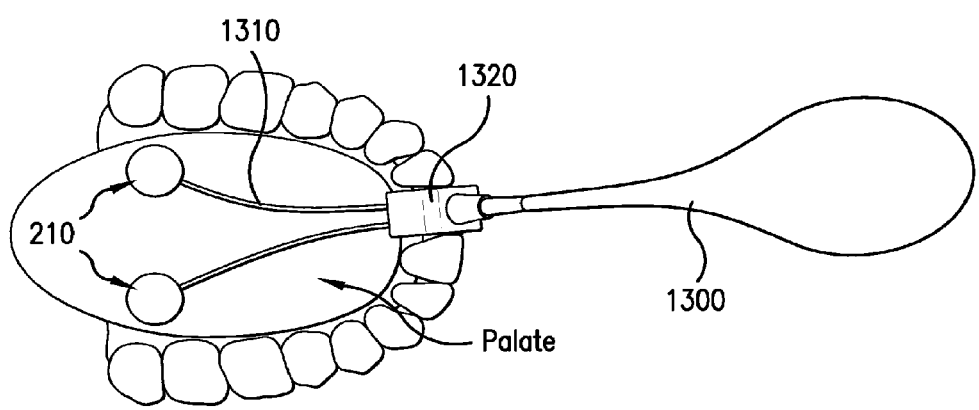

In one embodiment, node support 1310 preferably has a U-configuration to limit contact with the lips and to minimize obstruction of the oral cavity while providing sufficient strength. Further, node support 1310 is preferably about 0.5-1.5 mm thick to limit intrusiveness to the patient while providing sufficient strength. Additionally, node support 1310 may be particularly configured to allow proper placement of nodes 210 in the oral cavity to indicate the proper tongue position for a given sound. For example, as shown in the Figures, node support 1310 may be configured to extend particular distances from handle 1300, incline at particular angles with respect to handle 1300, or curve to follow certain contours to allow proper placement of nodes 210 for different sounds. As shown in FIG. 22, some embodiments may comprise node supports 1310 adapted to support multiple nodes 210. For example, as shown in FIG. 22, node support 1310 branches from handle 1300, extending outwardly and laterally from handle 1300 so that nodes 210 may positioned in the oral cavity to cue the proper lingual positions for the /g/, /k/, or /j/ sounds.

In some embodiments, means 220 for supporting and/or positioning nodes 210 may further comprise an alignment feature 1320. As shown in FIGS. 22, 26A, 26B, 27, 28, and 32, alignment feature 1320 may be configured to position device 200 with respect to various oral structures. Device 200 may be aligned with respect to various oral structures, including the inside of the upper dentition, outside of the upper dentition, or the alveolar ridge.

Provided below are descriptions of specific embodiments of handle-based devices 200 that comprise various node 210 configurations. It should be noted that the general description of handle-based devices 200 described above applies to the description of specific handle-based devises 200 described below. Thus, the below descriptions of the specific embodiments of handle-based devices 200 focus on particular features and configurations not described above.

/r/ Node Handle Device

Figure 23A:
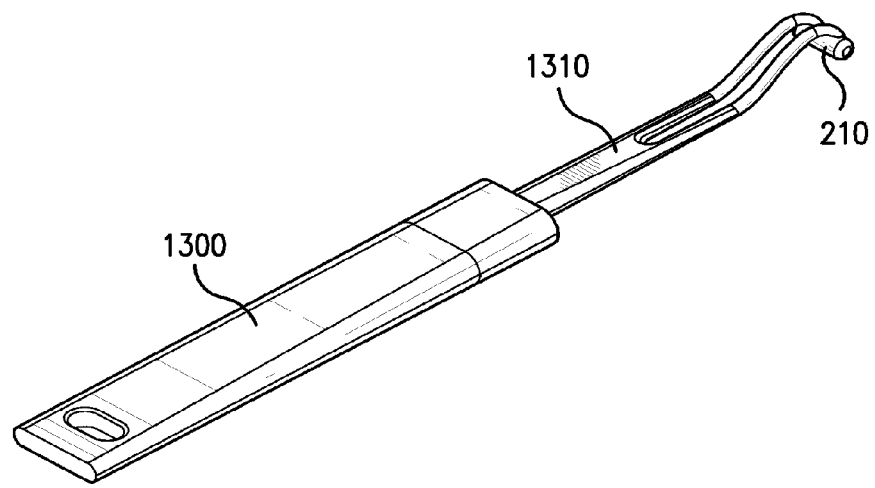
FIGS. 23A and 23B show an exemplary embodiment of an /r/ node device.
Figure 23B:
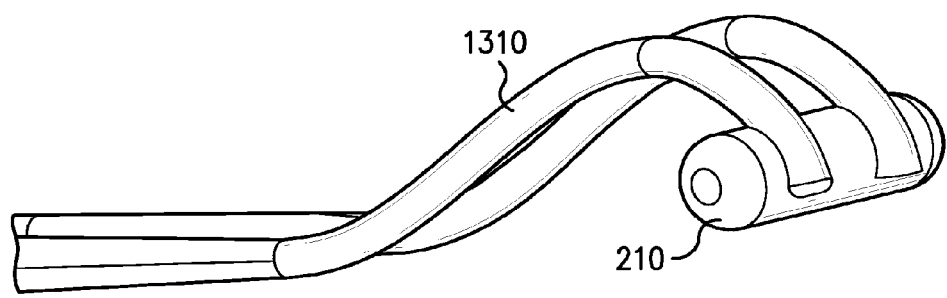

FIGS. 23A and 23B show an embodiment of a device 200 adapted to facilitate proper production of the /r/ sound. More particularly, device 200 is designed so that node 210 can maintain contact with the tongue as the tongue curls back in the mouth. As shown in this embodiment, device 200 comprises a handle 1300, node support 1310 extending from handle 1300, and node 210 disposed on the end of node support 1310. In this embodiment, node 210 is designed to be disposed below the palate to cue the progression of the tongue along a path that generates the /r/ sound. Thus, node support 1310 is designed to extend and curve upwardly outwardly from handle 1300 defining a long arc similar to the contour of the palate. The curved configuration of node support 1310 allows the tongue to move toward node 210 unimpeded by node support 1310. It is important that the tongue only contact node 210 in order to properly produce the /r/ sound.

In this embodiment, node 210 is preferably cylindrically shaped. In a preferred embodiment, cylindrically shaped node 210 has a diameter of 4 mm diameter and a length of 12 mm. Node 210 is preferably disposed on device 200 so that a longitudinal axis of the cylinder is transverse to a longitudinal axis of handle 1300. Thus, the tongue may contact the curved surface of the cylindrically shaped node 210. Alternatively, node 210 may have a rectangular shape and may be disposed so that the longitudinal axis of the rectangle is transverse to the longitudinal axis of handle 1300.

Device 200 may be positioned in the oral cavity by positioning node 210 below the palate and by maintaining node support 1310 in contact with the bottom of the front teeth. In order to properly produce the /r/ sound, a patient may contact the node 210C with their tongue tip and vocalize while moving the tongue tip posteriorly.

/r/ Spring Loaded Handle Device

Figure 24A:
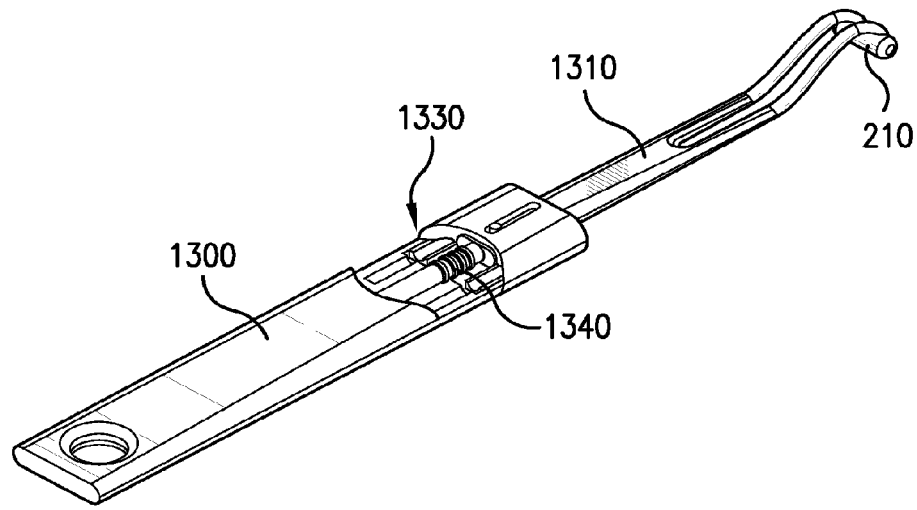
FIGS. 24A and 24B show an exemplary embodiment of an /r/ spring slide device.
Figure 24B:
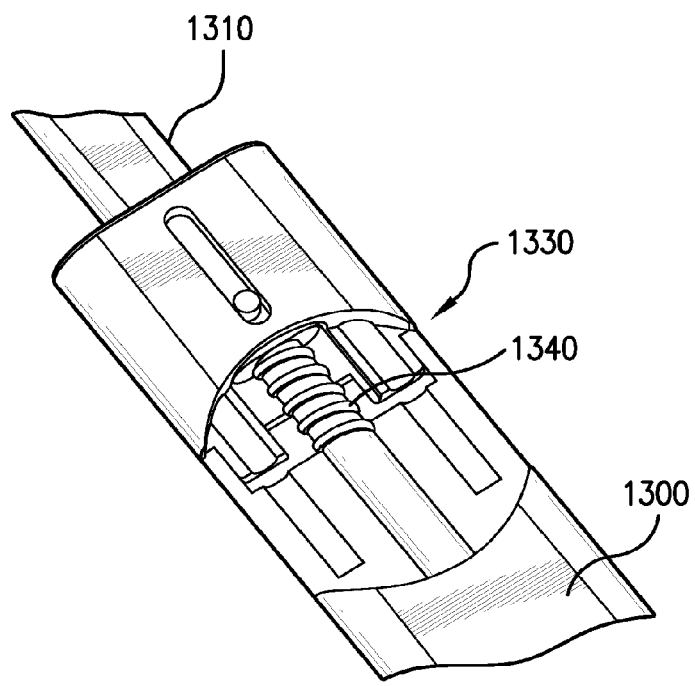

FIGS. 24A and 24B show an embodiment of a device 200 adapted to facilitate proper production of the /r/ sound that is substantially the same as the embodiment shown in FIGS. 23A and 23B, except for the configuration of handle 1300 and node support 1310. This embodiment is particularly useful for training the proper tongue movement required for the /r/ sound because it cues the progression of tongue movements required to properly produce the /r/ sound. As shown in FIGS. 24A and 24B, node support 1310 may be slidably connected to handle 1300 by a sliding mechanism 1330. Sliding mechanism 1330 allows node support 1310 to extend and/or retract with respect to handle 1300 with some resistance. As shown, sliding mechanism 1330 may preferably comprise a spring 1340 to resist relative movement between handle 1300 and node support 1310. Thus, sliding mechanism 1330 may maintain the relative position of node support 1310 and handle 1300 unless some degree of force is applied to cause relative movement. Further, slide mechanism 1330 may comprise a slide indicator 1350 to indicate relative movement relative movement between handle 1300 and node support 1310.

In proper production of the /r/ sound, the tongue rolls superiorly and posteriorly in the oral cavity below the palate. Device 200 may be positioned so that node 210 is disposed below the palate to cue the progression of the tongue along a path that generates the /r/ sound, according to whether the patient uses lingual retroflection or lingual retraction to typically generate his /r/ phoneme. As the tongue rolls or moves back and applies pressure on node 210 during production of the/r/sound, node 210 is allowed to move posteriorly by extension of node support 1310 with respect to handle 1300. Slide indicator 1350 provides some indication of the movement of node support 1310 with respect to handle 1300 so that a therapist can determine whether the patient is performing the proper tongue progression for the production of the/r/sound.

/s/ and /z/ Node Handle Device

Figure 25A:
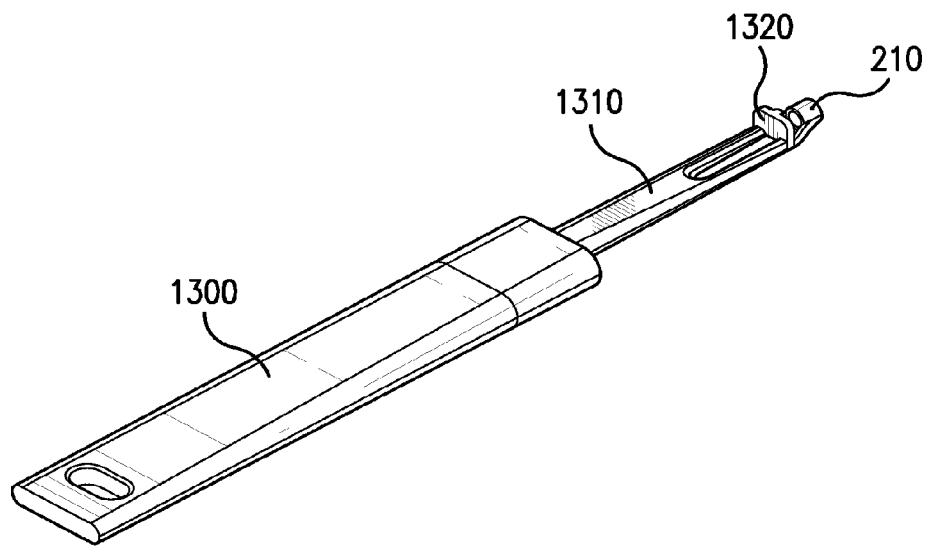
FIGS. 25A and 25B show an exemplary embodiment of a /s/ and /z/ node device.
Figure 25B:
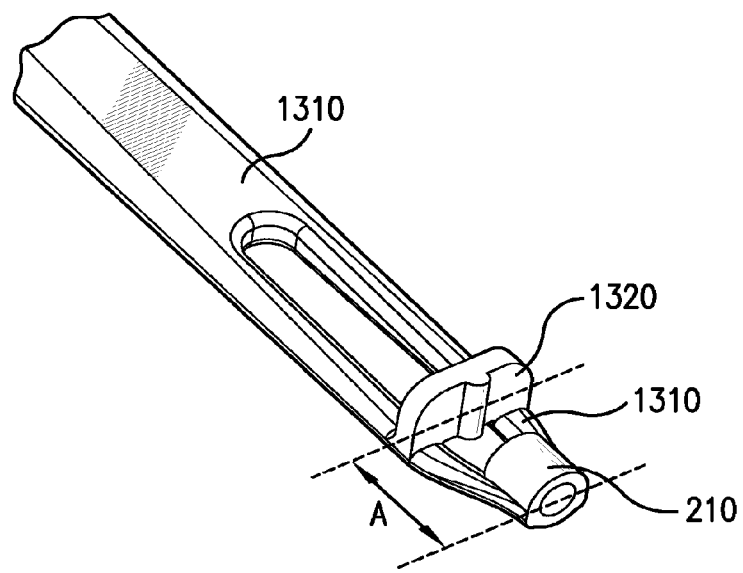

FIGS. 25A and 25B shows an embodiment of a device 200 adapted to facilitate proper production of the /s/ or /z/ sound. In the production of the /s/ and /z/ sounds the position of the tongue tip posterior to the front teeth is important for proper production of the sounds. Thus, node 210 is designed to be disposed a predetermined distance from the patient's teeth to cue the proper position of the tongue for the production of the /s/ and /z/ sounds.

As shown in this embodiment, device 200 comprises a handle 1300, node support 1310 extending from handle 1300, alignment feature 1320 disposed on node support 1310, and node 210 disposed on the end of node support 1310. As shown, handle 1300, node support 1310, alignment feature 1320, and node 210 may preferably be arranged linearly along a single axis. Node 210 is disposed on one end of node support 1310 opposite handle 1300. Alignment feature 1320 is disposed on node support 1310 between node 210 and handle 1300. Alignment feature 1320 is configured on node support 1310 so that the end of node support 1310 and node 210 extend into the oral cavity to indicate the proper tongue position to produce the /s/ or /z/ sound. As shown in FIG. 25B, dimension A measures the distance from alignment feature 1320 to the face of node 210. Dimension A corresponds to the distance that the tongue must maintain from the exterior of the top front teeth in order to produce the correct /s/ or /z/ sound. Thus, in a preferred embodiment, dimension A is about 4-15 mm. In order to produce a proper /s/ or /z/ sound, the tongue must about 4-15 mm from the exterior of the top front teeth. In a more preferred embodiment, dimension A is about 6-10 mm. In a most preferred embodiment, dimension A is about 8 mm.

As shown in this embodiment, alignment feature 1320 may be configured to register device 200 against the front of the teeth. Alignment feature 1320 may fit flush against the front teeth and may have small groove that fits between the exterior faces of the two front teeth. Alignment feature 1320 ensures that device 200 is properly oriented and positioned within the oral cavity to facilitate the production of speech sounds. As shown in this embodiment, node 210 may be configured in a tubular shape. As shown, a longitudinal axis of the tubular shape node 210 is parallel to a longitudinal axis of handle 1300. Thus, the tubular shape allows node 210 to position the tip of the tongue precisely. Further, the tubular shape minimizes resistance to airflow as the /s/ or /z/ sound is produced, which is important to minimize the effect on the production of proper speech sounds.

/Σ/ (sh) and /Z/ (ζη) Node Handle Device

Figure 26:
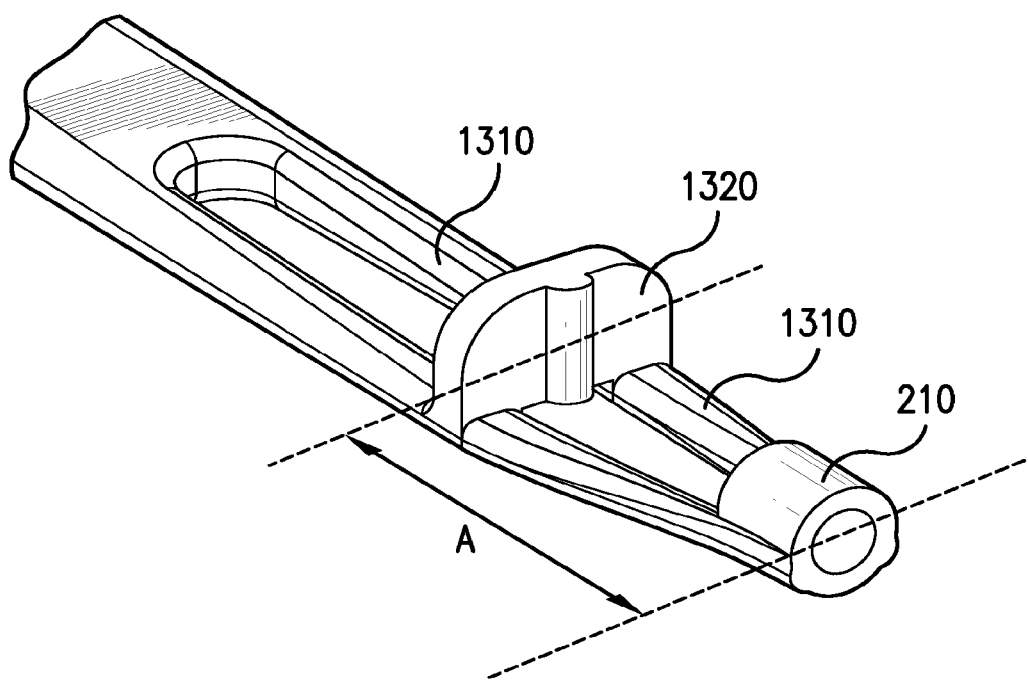
FIG. 26 show an exemplary embodiment of a /sh/ node device.

FIG. 26 shows an embodiment of a device 200 adapted to facilitate proper production of the /sh/ and /zh/ sounds. This embodiment of device 200 is the same as the embodiment of device 200 described with reference to FIG. 25, except the dimension A is different. In order to produce the /sh/ and /zh/ sounds, the tongue must be positioned more posteriorly than when producing the /s/ and /z/ sounds. Thus, in a preferred embodiment, dimension A is about 8-25 mm. In a more preferred embodiment, dimension A is about 15 mm.

/s/, /z/, and /Σ/ (sh), /Z/ (ζη) Dome-Shaped Node Handle Device

Figure 27:
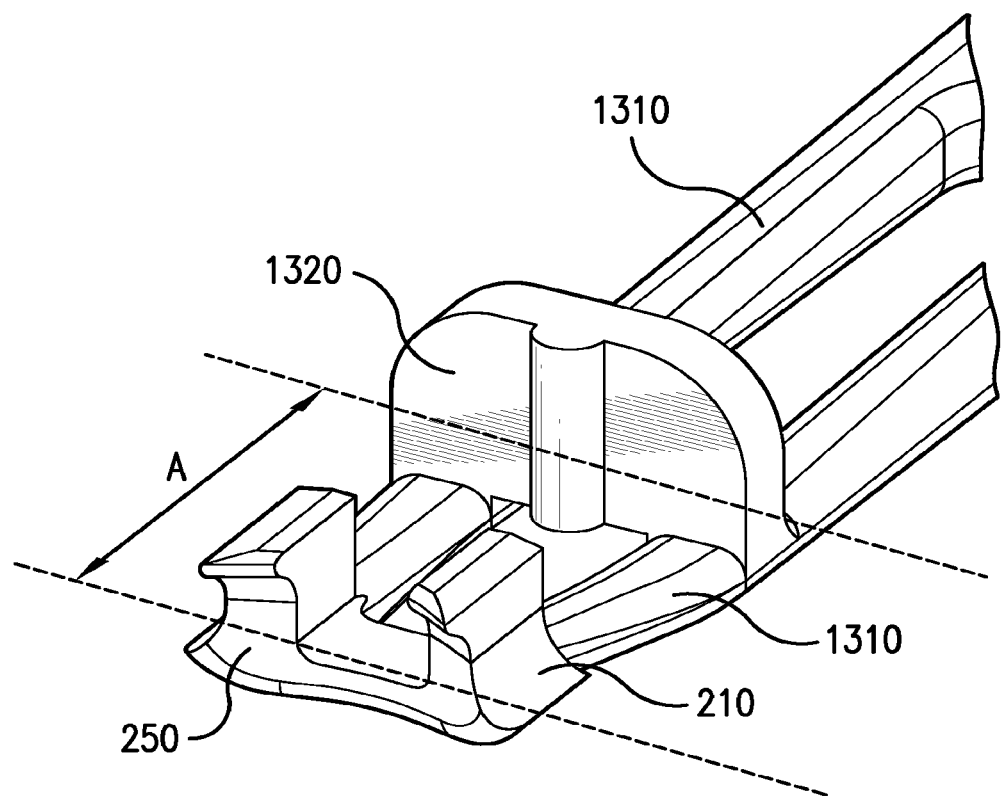
FIG. 27 show an exemplary embodiment of a /s/, /z/, /sh/, and /zh/ node device.

FIG. 27 shows another embodiment of a device 200 adapted to facilitate proper production of the /s/, /z/, /sh/, and /zh/ sounds. This embodiment of device 200 may be configured substantially the same as the embodiments of FIGS. 25 and 26. The only difference between the embodiment of FIG. 27 and the embodiments of FIGS. 25 and 26, is the shape of node 210. The embodiment of FIG. 27 provides an alternative to the tubular shape of the node 210 in embodiments of FIGS. 25 and 26. The nodes 210 of the embodiments of FIGS. 25 and 26 may be substituted with the node 210 of the embodiment of FIG. 27. As shown in FIG. 28, node 210 is generally U-shaped and has an inwardly-domed front face 250. Node 210 is disposed on one end of node support 1310 opposite handle 1300 such that the inwardly-dome face faces away from handle 1300. Further, node 210 is disposed on node support 1310 such that the open end of the U-shape (the legs) is directed upwardly from node support 1310. The U-shape and the inwardly-domed face 250 allow node 210 to position the tip of the tongue precisely and to minimize resistance to airflow.

/τΣ/ (ch) and /δZ/ (j) Node Handle Device

Figure 28A:
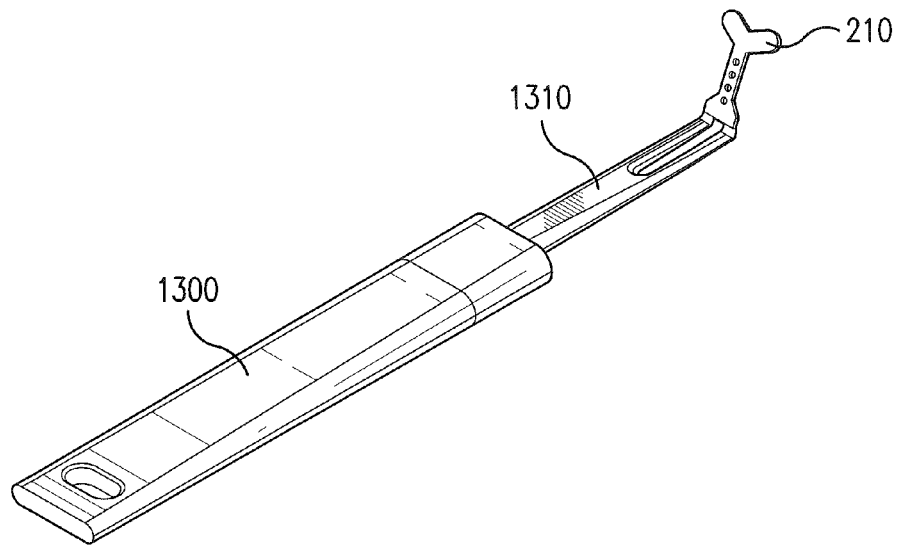
FIGS. 28A and 28B show an exemplary embodiment of a /ch/ node device.
Figure 28B:
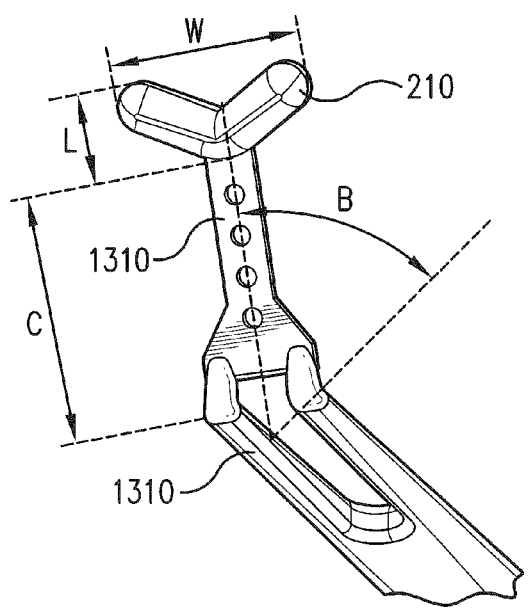

FIGS. 28A and 28B show an embodiment of device 200 adapted to facilitate proper production of the /τΣ/ (ch) and /δZ/ (j) sounds. As shown in this embodiment, device 200 may comprise a handle 1300, node support 1310 extending from handle 1300, and node 210 disposed on the end of node support 1310. In this embodiment, node 210 is designed to be in contact with the palate. Thus, node support 1310 is designed to be flexible. The flexibility of node support 1310 ensures that node 210 is in contact with the palate over a broad range of variation in anatomy. Further, in order to ensure that node 210 contacts the palate, node support 1310 is angled upwardly with respect to handle 1300. In a preferred embodiment, node support 1310 is angled with respect to handle 1300 by angle B from perpendicular and extends upwardly from the longitudinal axis of handle 1300 by a length C. The length C of the portion of node support 1310 that is angled upwardly from handle 1300 is important for proper placement of node 210 in the oral cavity. In a preferred embodiment, angle B is about 0-50 degrees from perpendicular and length C is about 8-25 mm. In a more preferred embodiment, angle B is about 25 degrees from perpendicular and length C is about 14 mm long.

As shown in this embodiment, node 210 may be generally V-shaped to closely mimic the surface area of the tongue that should be in contact with the palate when the /τΣ/ (ch) and /δZ/ (j) sounds are properly produced. In a preferred embodiment, node 210 has a width W (measured across the widest section) of about 5-25 mm and length L of about 2-15 mm. In a more preferred embodiment, node 210 has width W of about 15 mm and a length L of about 5 mm. In this embodiment, device 200 may be positioned by contacting the palate with the back of node 210 and by maintaining node support 1310 in contact with the bottom of the front teeth.

/l/ Node Handle Device

Figure 29A:
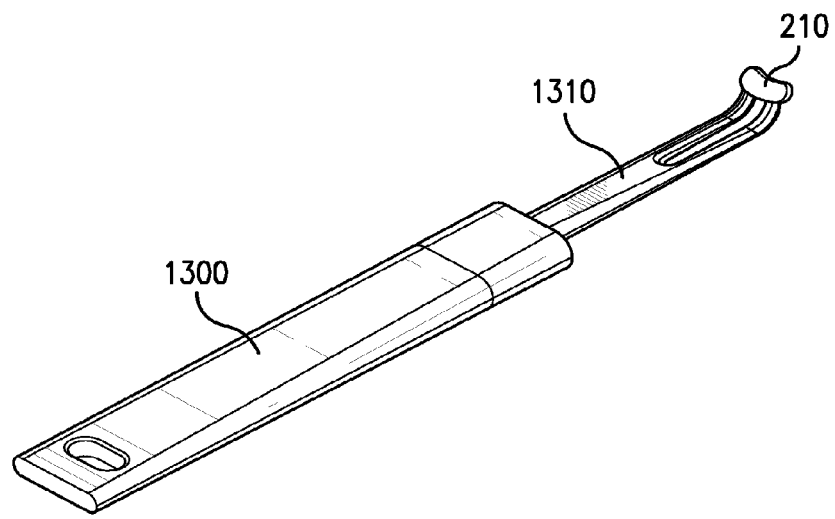
FIGS. 29A and 29B show an exemplary embodiment of a /l/ node device.
Figure 29B:
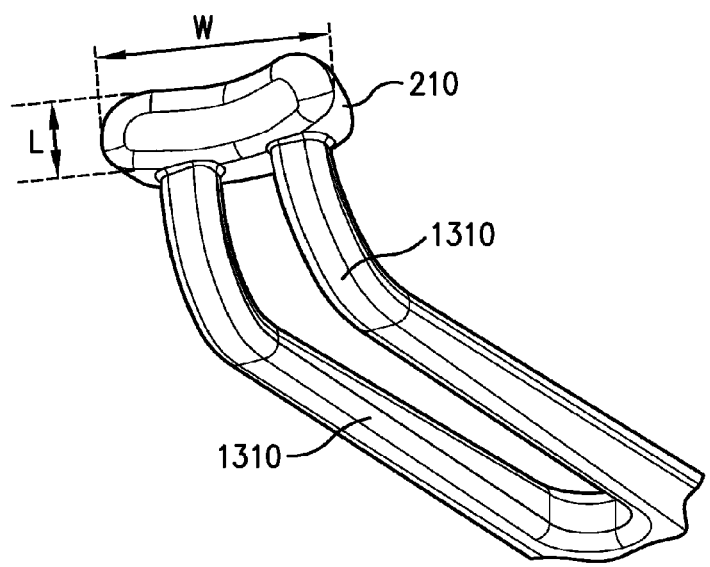

FIG. 29 shows an embodiment of a device 200 adapted to facilitate proper production of the /l/ sound. As shown in this embodiment, device 200 may comprise a handle 1300, node support 1310 extending from handle 1300, and node 210 disposed on the end of node support 1310. In this embodiment, node 210 is designed to rest on the alveolar ridge. Thus, node support 1310 is designed to be angled upwardly with respect to handle 1300.

Node 210 has an inwardly-domed face that mimics the surface area of the tongue that contacts the alveolar ridge or teeth during normal sound production. In a preferred embodiment, node 210 has a rectangular shape and has a width W of about 3-20 mm and a length L of about 2-10 mm. In a more preferred embodiment, node 210 has a width W of about 10 mm and a length L of about 5 mm. In this embodiment, device 200 may be positioned by contacting the alveolar ridge with the back of node 210 and by maintaining node support 1310 in contact with the bottom of the front teeth.

Handle Device Kit

In order to treat or train various classes of consonant sounds in accordance with the methods 100 and devices 200 described herein, a therapist must be able to cue various tongue positions during the production of speech sound. To be able to cue the various tongue positions for the proper production of different speech sounds, a therapist may need to employ various node 210 configurations to provide the proper tactile feedback. Thus, in accordance with another aspect of the invention, provided is a kit 2000 containing one or more devices 200 for providing the proper tactile feedback for the production of a plurality of speech sounds.

Figure 30:
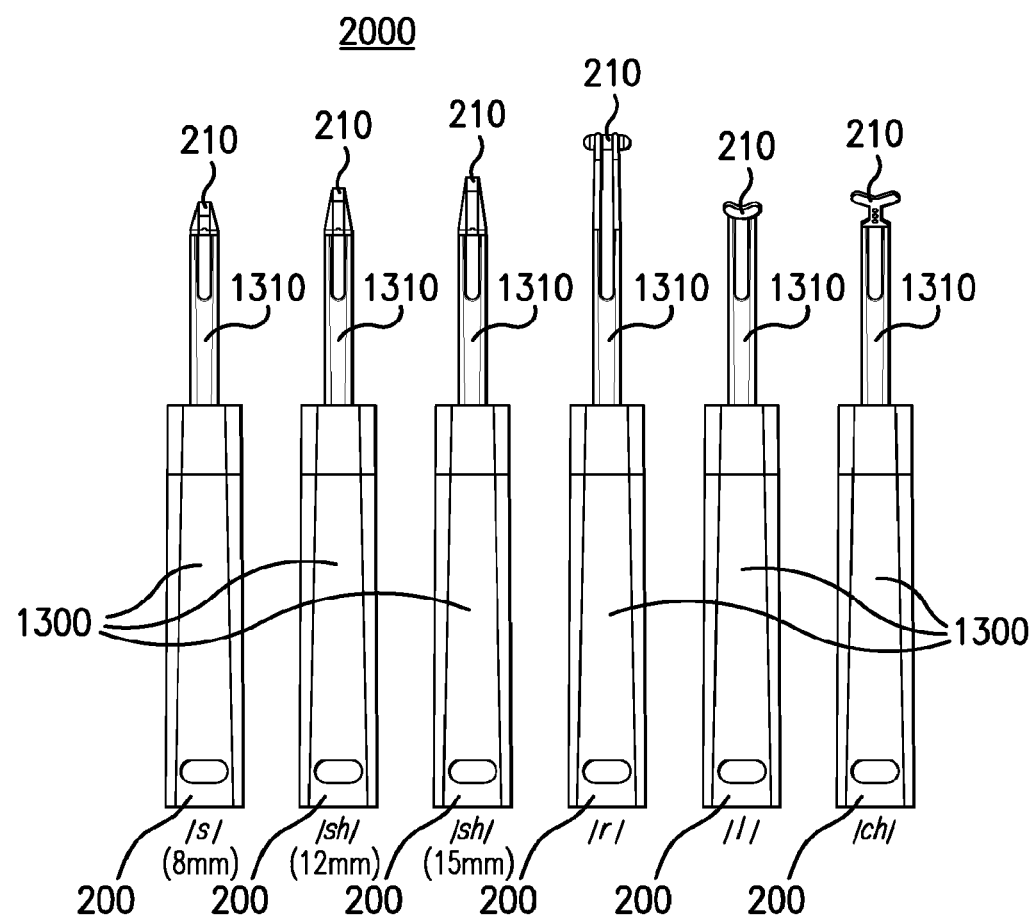
FIG. 30 shows an exemplary embodiment of a kit of devices.

In one embodiment, as shown in FIG. 30, a kit 2000 may comprise a plurality of devices 200 of the types disclosed herein. Each of the devices may be configured to facilitate proper production of a particular speech sound or a particular set of speech sounds. As shown, each device 200 in kit 2000 may comprise a handle 1300, node support 1310 extending from handle 1300, and node 210 disposed on the end of node support 1310. Further, each device in kit 2000 may be specifically configured to provide proper tactile feedback for a particular speech sound or a particular set of speech sounds, as described in detail above with reference to particular device 200 embodiments. For example, as shown in FIG. 30, kit 2000 may comprise a device 200 for facilitating proper production of the /s/ and /z/ sounds, a device 200 for facilitating proper production of the /sh/ and /zh/ sounds, a device 200 for facilitating proper production of the /r/ sound, a device 200 for facilitating proper production of the /l/ sound, and a device 200 for facilitating proper production of the /τΣ/ (ch) and /δZ/ (j) sounds. However, it should be understood that kit 200 may comprise more devices, fewer devices, or different devices than those shown in this embodiment.

Figure 31:
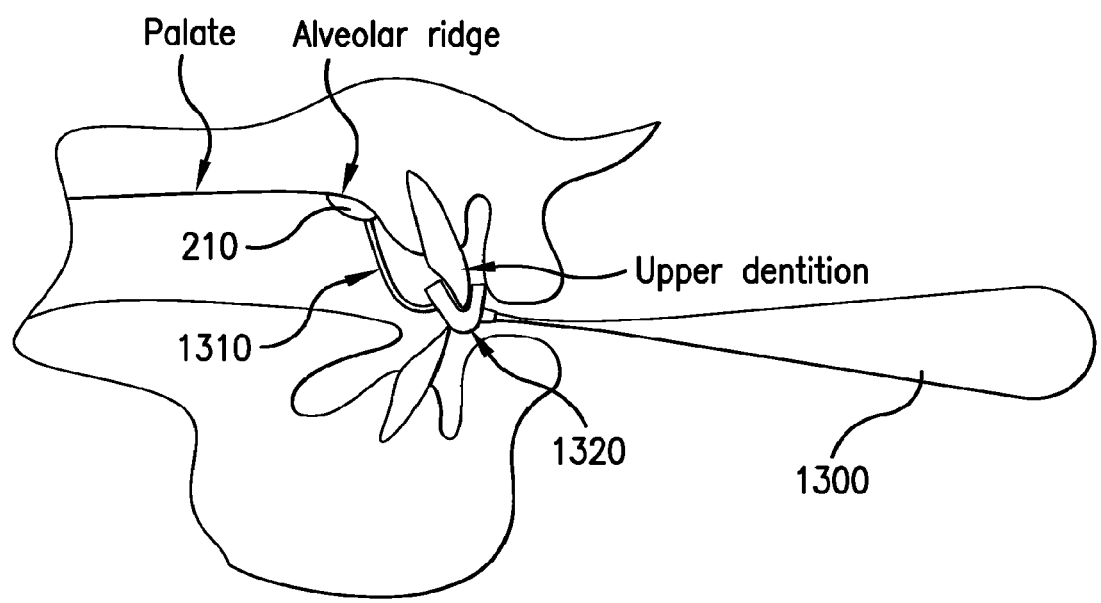
FIG. 31 shows an exemplary embodiment of a detachable handle device.

In another embodiment, a kit 2000 may comprise one or more handles 1300, a plurality of different node supports 1310, and a plurality of different nodes 210. Each of the plurality of node supports 1310 and each of the plurality of nodes 210 may be specifically configured to provide proper tactile feedback for a particular speech sound or a particular set of speech sounds. Further, each of the node supports 1310 may be adapted to be removably attached to the one or more handles 1300, and each of the nodes 210 may be adapted to be removably attached to the node supports 1310. Thus, a therapist may attach a particular node support 1310 to a handle 1300 and attach a particular node 210 to the node support 1310. A therapist may use kit 2000 to assemble various devices 200 configured to provide proper tactile feedback for different speech sounds. FIG. 31, shows an embodiment of a device 200 comprising disposable nodes 210 that may be removably attached to node support 1310.

Alternatively, kit 2000 may provide particular node supports 1310 in combination with particular node 210 configurations. In such an embodiment, kit 2000 may contain a plurality node support 1310 and node 210 combinations, where each node support 1310 and node 210 combination is specifically configured to provide proper tactile feedback for a particular speech sound or a particular set of speech sounds. In such an embodiment, each of the node support 1310 and node 210 combinations may be removably attached to the one or more handles in kit 2000. Thus, a therapist may use kit 2000 to assemble various devices 200 configured to provide proper tactile feedback for different speech sounds.

What is claimed is:

1. A method of teaching a person to pronounce a particular sound, which comprises:
   providing at least one sound training device comprising a handle, a node support and one or more nodes for indicating proper positioning of the person's tongue for accurate pronunciation of the particular sound, with the node support configured and dimensioned (a) to provide tactile feedback to the person at its respective node location(s) on the node support with the feedback signaling proper positioning of the tongue for accurate pronunciation of the particular sound, and (b) to limit intrusiveness in the person's mouth while providing sufficient strength to support the one or more nodes;
   providing at least one of the one or more nodes with a sensor mounted thereon, with the sensor positioned and dimensioned for sensing lingual contact of the person's tongue with or near the node, providing a signal based such contact, and transmitting the signal to a computer; and
   providing the device with registration features for positioning the device in an appropriate location in the person's oral cavity such that the person's tongue is able to freely navigate to contact the one or more nodes and be positioned for making the particular sound with the location being dependent on the particular sound to made,
   wherein the method provides a first device comprising a cylindrical node configured to be positioned in a medial location inferior to the person's palate to provide tactile feedback for the proper tongue position corresponding to the /r/ sound;
   wherein, when the tongue is so positioned, the sound training device provides tactile feedback to the person to assist in proper and accurate pronunciation of the particular sound, and wherein the computer includes software that monitors contact of the tongue with the sensor(s) that are mounted on and are no larger than the node(s) and provides interactive feedback including one or more of:
   real time on-screen visualization of lingual contacts with the one or more nodes;
   game style positive reinforcement based on progress, data collection or statistical analysis;
   playback of recorded verbal reproductions;
   an indication of the status of patient speech productions; and
   pre-recorded phoneme productions to encourage greater accuracy via imitation;
   providing one or more additional devices selected from a group of devices including:
   a second device comprising a node configured to be positioned in a location on the person's alveolar ridge to provide tactile feedback for the proper tongue position corresponding to the /l/, /t/, or /d/ sound;
   a third device comprising a pair of nodes configured to be positioned in lateral posterior locations on either side of the person's palate to provide tactile feedback for the proper tongue position corresponding to the /k/ or /g/ sound;
   a fourth device comprising a pair of nodes configured to be positioned in lateral anterior locations on either side of the person's palate to provide tactile feedback for the proper tongue position corresponding to the l) l sound;
   a fifth device comprising a node configured to be positioned in an anterior location inferior to the person's palate to provide tactile feedback for the proper tongue position corresponding to the /s/, /z/, ILI (sh), or /Z/ (Qr\) sounds; and
   a sixth device comprising a node configured to be positioned in an anterior location on the person's palate to provide tactile feedback for the proper tongue position corresponding to the lx LI (ch) or /8Z/ (j) sound,
   wherein the devices are provided in a kit that includes a common handle that can be used for separately and sequentially holding each device, and
   wherein each handle includes a node support and an alignment guide located thereon for proper positioning of the device on the person's palate.

2. The method of claim 1, wherein each of the devices with a non-English language speech sound that is similar to the English speech sound to which the device corresponds.

3. The method of claim 1, wherein the person is hearing impaired.

4. The method of claim 1, wherein the person suffers from acquired apraxia of speech, developmental apraxia of speech, or dysarthria.

5. The method of claim 1, wherein the person is learning to speak sounds that are foreign to his or her native language.

6. The method of claim 1, wherein the at least one sound training device is selected from a kit that includes each of the first, second, third, fourth, fifth and sixth devices with the particular device selected for teaching how to pronounce the desired sound, and wherein each device includes a handle that permits holding and positioning of the one or more nodes of the selected devices in the person's oral cavity so as to automatically place the one or more nodes in correspondence with proper lingual positions for production of the particular sound.

7. The method of claim 1, wherein the one or more nodes are configured in a spring or coil shape, or supported on a slide that allows the one or more nodes to move in response to pressure applied by the person's tongue.

8. The method of claim 1, wherein the six devices are provided in a kit that includes a common handle that can be used for separately and sequentially holding each device.

9. The method of claim 1 which further comprises prompting the person to make the particular speech sound by contacting the node or nodes with his or her tongue after positioning the device and one or more nodes in a location in the person's oral cavity corresponding to the appropriate lingual position for a particular speech sound.

\* \* \* \* \*

UNITED STATES PATENT AND TRADEMARK OFFICE
CERTIFICATE OF CORRECTION

| | | |
|---|---|---|
| PATENT NO. | : 9,711,063 B2 | Page 1 of 1 |
| APPLICATION NO. | : 15/046415 | |
| DATED | : July 18, 2017 | |
| INVENTOR(S) | : Penake et al. | |

It is certified that error appears in the above-identified patent and that said Letters Patent is hereby corrected as shown below:

In the Claims

Column 22:
Line 25, after "proper tongue position corresponding to the", delete "l) l" and insert -- *l) l* --.
Line 41, after "2. The method of claim 1, wherein each of the devices", insert -- associates --.

Signed and Sealed this
Twenty-second Day of August, 2017

Joseph Matal
*Performing the Functions and Duties of the
Under Secretary of Commerce for Intellectual Property and
Director of the United States Patent and Trademark Office*